US012788240B2

(12) United States Patent
Terabe et al.

(10) Patent No.: US 12,788,240 B2
(45) Date of Patent: Nov. 10, 2026

(54) STORAGE MEDIUM STORING OPTOMETRY CONTROL PROGRAM AND SUBJECTIVE OPTOMETRY SYSTEM

(71) Applicant: NIDEK CO., LTD., Gamagori (JP)

(72) Inventors: Hirohisa Terabe, Gamagori (JP); Taeko Horino, Gamagori (JP); Arisa Simazaki, Gamagori (JP)

(73) Assignee: NIDEK CO., LTD.

( * ) Notice: Subject to any disclaimer, the term of this patent is extended or adjusted under 35 U.S.C. 154(b) by 336 days.

(21) Appl. No.: 18/319,372

(22) Filed: May 17, 2023

(65) Prior Publication Data

US 2023/0284896 A1 Sep. 14, 2023

Related U.S. Application Data

(63) Continuation of application No. PCT/JP2021/041922, filed on Nov. 15, 2021.

(30) Foreign Application Priority Data

Nov. 20, 2020 (JP) ................................ 2020-193730
Dec. 4, 2020 (JP) ................................ 2020-201880
Jul. 10, 2021 (WO) ................. PCT/JP2021/037111

(51) Int. Cl.
*A61B 3/032* (2006.01)
*A61B 3/028* (2006.01)
(Continued)

(52) U.S. Cl.
CPC .............. *A61B 3/032* (2013.01); *A61B 3/028* (2013.01); *G16H 40/67* (2018.01); *G16H 80/00* (2018.01)

(58) Field of Classification Search
None
See application file for complete search history.

(56) References Cited

U.S. PATENT DOCUMENTS

2011/0116047 A1* 5/2011 Polat .................... A61B 3/0033 351/239
2014/0211164 A1* 7/2014 Nakamura ............ A61B 3/032 351/239
(Continued)

FOREIGN PATENT DOCUMENTS

JP 1994189913 A 7/1994
JP 2008054928 A 3/2008
(Continued)

OTHER PUBLICATIONS

Communication Art 94(3) for EPC received in Appl. No. 21 894 596.2 dated May 22, 2025, 7 pgs.
(Continued)

*Primary Examiner* — Sharrief I Broome
*Assistant Examiner* — Journey F Sumlar
(74) *Attorney, Agent, or Firm* — Yusuke Hirai; Best Mode IP Law, PLLC

(57) ABSTRACT

A non-transitory, computer readable, storage medium stores a self-optometry control program that is executed by a first information processing device and includes a self-optometry program. The self-optometry program causes the first information processing device to perform executing a calling operation based on a calling instruction and setting an examination timing for an assistance operation such that the assistance operation starts from an examination item that was performed at a timing the calling instruction was inputted.

12 Claims, 6 Drawing Sheets

(51) Int. Cl.
*G16H 40/67* (2018.01)
*G16H 80/00* (2018.01)

(56) References Cited

U.S. PATENT DOCUMENTS

| | | | | |
|---|---|---|---|---|
| 2014/0268060 | A1* | 9/2014 | Lee | G02C 13/005 351/241 |
| 2016/0317025 | A1* | 11/2016 | Lee | A61B 5/0022 |
| 2017/0135572 | A1* | 5/2017 | Takii | A61B 3/04 |
| 2018/0192868 | A1 | 7/2018 | Sakurada et al. | |
| 2020/0170506 | A1 | 6/2020 | Higuchi | |

FOREIGN PATENT DOCUMENTS

| | | | |
|---|---|---|---|
| JP | 2017143992 | A | 8/2017 |
| JP | 2019062978 | A | 4/2019 |
| JP | 2020018712 | A | 2/2020 |
| WO | WO 2020050496 | A | 3/2020 |

OTHER PUBLICATIONS

International Search Report of PCT/JP2021/041922, Issued on Feb. 15, 2022.
Written Opinion of PCT/JP2021/041922, Issued on Feb. 15, 2022.

* cited by examiner

STORAGE MEDIUM STORING OPTOMETRY CONTROL PROGRAM AND SUBJECTIVE OPTOMETRY SYSTEM

CROSS REFERENCE TO RELATED APPLICATIONS

This application is a continuation application of International Patent Application No. PCT/JP2021/041922 filed on Nov. 15, 2021, which designated the U.S. and claims the benefit of priority from Japanese Patent Application No. 2020-193730 filed on Nov. 20, 2020, Japanese Patent Application No. 2020-201880, filed on Dec. 4, 2020, and International Patent Application PCT/JP2021/037111 filed on Oct. 7, 2021. The entire disclosure of all of the above applications is incorporated herein by reference.

TECHNICAL FIELD

The present disclosure relates to a storage medium storing an optometry control program executed by a subjective optometry system and the subjective optometry system.

BACKGROUND ART

A subjective optometry device has been known for measuring optical characteristics such as refractive power of a subject eye by presenting an examination target to the subject eye through an optical element in front of the subject eye. For example, a subjective optometry device disclosed in JP 2020-18712 A includes a refractive power measuring unit, an examination target presenting unit, and a controller. The refractive power measuring unit selects an optical element to be placed through an examination window from among a plurality of optical elements included in a correction optical system by a driver that switches the optical elements. The examination target presenting unit switches the examination targets each of which is presented to the subject eye. The controller detects a user operation on an operation panel and transmits a driving signal to the refractive power measuring unit and the examination target presenting unit based on the detected user operation.

SUMMARY

In a conventional subjective optometry device, it was necessary for an examiner to be present with the examinee and input instructions for the next operation of the subjective optometry device based on responses from the examinee who visually recognized a visual target. Therefore, it was difficult for such a conventional subjective optometry device to execute subjective optometry smoothly while reducing the burden on the examiner.

One objective of the present disclosure is to provide a storage medium storing a subjective optometry control program and a subjective optometry system that enable it possible to perform a subjective optometry more smoothly.

In view of the above, the present disclosure includes the following features.

(1) A non-transitory, computer readable, tangible storage medium stores an optometry control program for a subjective optometry system including a subjective optometry device and a first information processing device connected to the subjective optometry device. The subjective optometry device includes a correction optical system that changes an optical characteristic of a visual target light flux presented to a subject eye and a visual target presentation unit that is configured to present a visual target to the subject eye. The subjective optometry device subjectively measures an optical characteristic of the subject eye. The program being executed by the first information processing device and comprising:

- a self-optometry program that causes a self-optometry to proceed automatically based on a response from an examinee.

The self-optometry program, when executed by the first information processing device, causes the first information processing device to perform:

- controlling the correction optical system and the visual target presentation unit to perform a plurality of examination items in accordance with a progress procedure for the self-optometry that automatically proceeds;
- acquiring a response inputted by the examinee who visually recognized the presented visual target; and
- executing an assistance operation to assist in a progress of the self-optometry when a problem occurs during the progress of the self-optometry.

The self-optometry program further causes the first information processing device to perform:

- receiving, from the examinee, an input of a calling instruction for executing a calling operation to call for an assistant;
- executing the calling operation based on the received calling instruction received; and
- setting, based on the received calling instruction, an examination timing for the assistance operation such that the assistance operation starts from an examination item among the plurality of examination items that was performed at a timing the calling instruction was inputted.

(2) An non-transitory, computer readable, tangible storage medium stores an optometry control program for a subjective optometry system including a subjective optometry device and a first information processing device connected to the subjective optometry device. The subjective optometry device includes a correction optical system that changes an optical characteristic of a visual target light flux presented to a subject eye and a visual target presentation unit that is configured to present a visual target to the subject eye. The subjective optometry device subjectively measures an optical characteristic of the subject eye. The program is executed by the first information processing device and includes:

- a self-optometry program that causes a self-optometry to proceed automatically based on a response from an examinee.

The self-optometry program, when executed by the first information processing device, causes the first information processing device to perform:

- controlling the correction optical system and the visual target presentation unit to perform a plurality of examination items in accordance with a progress procedure for the self-optometry that automatically proceeds;
- acquiring a response inputted by the examinee who visually recognized the presented visual target; and
- executing an assistance operation to assist in a progress of the self-optometry when a problem occurs during the progress of the self-optometry.

The self-optometry program further causes the first information processing device to perform:

- receiving an input of an execution instruction for executing the assistance operation; and
- restricting an input of the response that is inputted after receiving the execution instruction.

(3) A non-transitory, computer readable, tangible storage medium stores an optometry control program for a subjective optometry system including a subjective optometry device and a first information processing device connected to the subjective optometry device. The subjective optometry device includes a correction optical system that changes an optical characteristic of a visual target light flux presented to a subject eye and a visual target presentation unit that is configured to present a visual target to the subject eye, the subjective optometry device subjectively measuring an optical characteristic of the subject eye. The program is executed by the first information processing device and includes:

a self-optometry program that causes a self-optometry to proceed automatically based on a response from an examinee.

The self-optometry program, when executed by a controller of the first information processing device, causes the first information processing device to perform:

controlling the correction optical system and the visual target presentation unit to perform a plurality of examination items in accordance with a progress procedure for the self-optometry that automatically proceeds;

acquiring a response inputted by the examinee who visually recognized the presented visual target; and executing an assistance operation to assist in a progress of the self-optometry when a problem occurs during the progress of the self-optometry.

The self-optometry program further causes the first information processing device to perform:

receiving an input of an execution instruction for executing the assistance operation;

restricting, until the execution instruction is inputted, at least a part of an operation input from an examiner controller that is configured to control the subjective optometry device by an examiner as the assistant; and removing the restriction on the operation input from the examiner controller when receiving the execution instruction.

(4) A subjective optometry system includes:

a subjective optometry device; and a first information processing device connected to the subjective optometry device.

The subjective optometry device includes a correction optical system that changes an optical characteristic of a visual target light flux presented to a subject eye and a visual target presentation unit that is configured to present a visual target to the subject eye.

The subjective optometry device is configured to subjectively measure an optical characteristic of the subject eye.

The first information processing device is configured to execute a self-optometry program that causes a self-optometry to proceed automatically based on a response from an examinee.

The first information processing device is, when executing the self-optometry program, configured to:

control the correction optical system and the visual target presentation unit to perform a plurality of examination items in accordance with a progress procedure for the self-optometry that automatically proceeds;

acquire a response inputted by the examinee who visually recognized the presented visual target; and execute an assistance operation to assist in a progress of the self-optometry when a problem occurs during the progress of the self-optometry.

The first information processing device, when executing the self-optometry program, is further configured to:

receive, from the examinee, an input of a calling instruction for executing a calling operation to call for an assistant;

execute the calling operation based on the received calling instruction; and set, based on the received calling instruction, an examination timing for the assistance operation such that the assistance operation starts from an examination item among the plurality of examination items that was performed at a timing the calling instruction was inputted.

According to the optometry control program and the subjective optometry system disclosed herein, a subject optometry can be executed performed smoothly.

DESCRIPTION OF EMBODIMENTS

Figure 1:
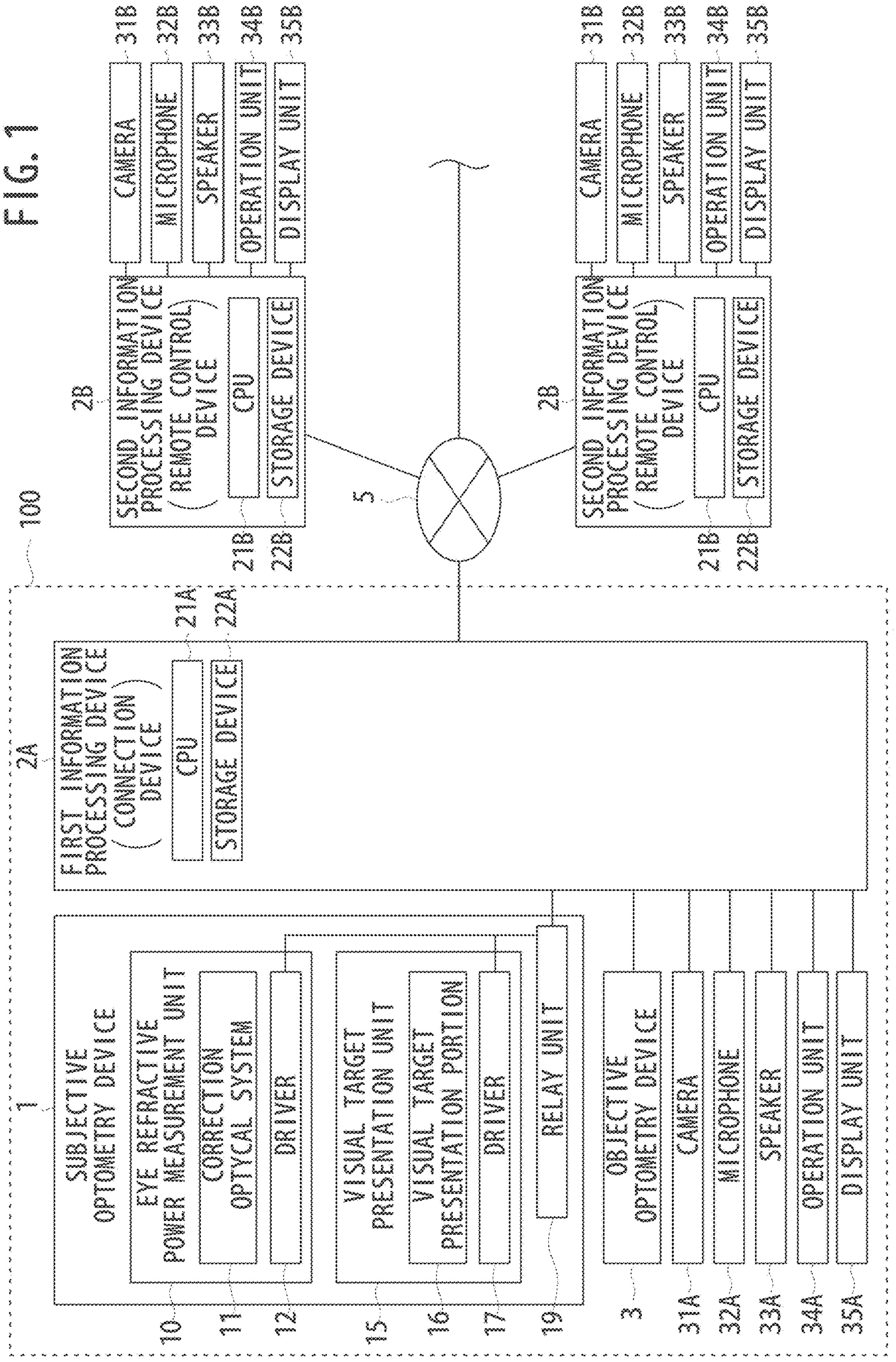
FIG. 1 is a block diagram showing a configuration of a subjective optometry system 100.

Next, an embodiment of the present invention will be described with reference to drawings. Note that the following heading items with < > can be used independently or in association with each other.

<Overview>

The subjective optometry system disclosed in the present disclosure includes the subjective optometry device and the first information processing device. The subjective optometry device includes the correction optical system that changes an optical characteristic of a visual target light flux presented to the subject eye, and the target presentation unit that presents a visual target to the subject eye. The subjective optometry device is used to subjectively measure the optical characteristic of the subject eye. The first information processing device is an information processing device connected to the subjective optometry device (hereinafter, the first information processing device may also be referred to as a "connection device"). The self-optometry program is a program that automatically proceeds with an optometry based on responses input by the examinee.

The self-optometry program executes a subjective optometry progress step, a response acquisition step, a correction value storage step, and a subjective optometry assistance step by the control unit of the first information processing device. In the subjective optometry progress step, the first information processing device sequentially outputs a plurality of presentation instruction signals to the subjective optometry device for presenting the visual target to the examinee in accordance with at least a progress procedure along which the subjective optometry automatically proceeds (i.e., along the progress procedure). It should be noted that in the subjective optometry progress step, the first information processing device may control the correction optical system and the target presentation unit to execute a plurality of examination items based on the progress procedure for the subjective optometry which automatically proceeds. At the response acquisition step, the first information processing device acquires responses inputted by the examinee who visually recognized the presented visual target. In the correction value storage step, the first information processing device stores a correction value of the optical characteristic of the subject eye, which is obtained based on the answers acquired at the response acquisition step and the optical characteristics of the presented visual target and of the visual target light flux presented by the subjective optometry device. In the subjective optometry assistance step, the first information processing device executes an assistance operation to assist in the auto-subjective optometry when a problem occurs during the auto-subjective optometry.

According to the subjective optometry system disclosed herein, even if an examiner does not proceed with the examination, an appropriate eye examination for an examinee can be performed by executing the self-optometry program. Furthermore, if a problem occurs during the self-optometry, the assistance operation for assisting in the self-optometry is executed. In other words, a function for assisting in the progress of the self-optometry is included in functions of the self-optometry program. Therefore, for example, during the execution of the self-optometry program, at least one of assistance operations for the self-optometry, such as providing an advice from the examiner, is executed. Thus, the subjective optometry can be properly performed with reduced burden on the examiner.

Note that various devices can be used as the first information processing device that executes the optometry control program. For example, a personal computer (PC) may be used as the first information processing device. Alternatively, a server, a mobile terminal, or a smartphone may be used as the first information processing device.

The first information processing device may be formed by combining two or more of a plurality of devices. For example, the first information processing device may be formed of a device, such as a personal computer, and a dedicated controller having a controlling unit and a memory. Of course, the dedicated controller itself may serve as the first information processing device by having functions of a device such as a personal computer equipped with a CPU.

The storage device for storing the optometry control program may be appropriately selected. For example, the optometry control program may be stored in a memory built into the first information processing device or in a detachable storage device for the first information processing device. The optometry control program may also be stored in a memory built into the above-described dedicated controller. Additionally, the optometry control program may be stored in multiple storage devices.

In the self-optometry assistance step, when a predetermined condition is met during the execution of the self-optometry, or when an instruction for executing the assistance operation is input, the assistance operation for assisting in the self-optometry may be executed. In this case, when the examinee is unable to perform the self-optometry due to certain circumstances, the assistance operation for the self-optometry is performed appropriately.

Note that the conditions in the self-optometry for executing the assistance operation may be appropriately selected. For example, the control unit may determine that the condition for executing the assistance operation is met when a predetermined time has elapsed without receiving an input of a response from the examinee. Alternatively, the control unit may determine that the condition for executing the assistance operation is met when a response is inappropriately input by the examinee. The method for determining whether the response is inappropriate may be appropriately selected. For example, the control unit may determine that the input response is inappropriate if the response does not meet a predetermined response condition (e.g., if a response different from candidate responses expected to receive from the examinee is input, if the same responses are input consecutively more than a predetermined number of times, or if the number of responses exceeds the number of responses expected to be input from the examinee).

The assistance operation executed at the self-optometry assistance step may include a call operation for calling for an examiner. In this case, when a problem occurs during the self-optometry, the examiner is called so that a subsequent examination can properly proceed.

The self-optometry assistance step may include a manual progress step in which a presentation instruction signal for advancing at least a part of the progress procedure is outputted to the subjective optometry device in response to receiving an instruction input from an examiner. In this case, the examiner may manually advance at least an examination step at which a problem occurred among the progress procedure that are planned to be performed during the self-optometry. Therefore, the optometry for the examinee can be more appropriately supported.

The self-optometry assistance step may include a correction value modification step to modify at least one of correction values stored during the self-optometry in response to receiving an instruction inputted by an examiner. In this case, for example, if a correction value that failed to be measured during the self-optometry exists, the correction value can be modified based on the examiner's decision. Therefore, the optometry for the examinee may smoothly proceeds.

The self-optometry assistance step may include a procedure omission step to omit at least a part of the progress procedure in response to receiving an instruction inputted by an examiner. In this case, the examiner can omit an unnecessary step from the predetermined steps. Therefore, the optometry for the examinee can proceed smoothly.

The method for inputting the instruction by the examiner to omit at least a part of the steps may be appropriately selected. For example, the examiner may input, into the first information processing device, a selection instruction for omitting a test from among the multiple tests executed in accordance with the progress procedure. In this case, the control unit of the first information processing device may omit the selected test from the tests. Also, the examiner may input, into the first information processing device, a timing for resuming the self-optometry, which is temporarily stopped, as a timing subsequent to the omitted step. In this case, the control unit of the first information processing device may omit a part of the steps by resuming the self-optometry from the inputted timing which is set after the omitted step.

The self-optometry assistance step may include a proxy response acquisition step. In the proxy response acquisition step, the control unit acquires, in response to an instruction inputted by an examiner, a response from an examinee who has visually recognized a visual target that was presented in accordance with the progress procedure at the self-optometry step. In this case, during the process in which visual targets are presented to the examinee in an order according to the progress procedure of the self-optometry, the examiner can hear the responses from the examinee who has recognized the visual target and enter the responses heard from the examinee. Therefore, even if the examinee is not familiar with a way of responding in the self-optometry, the examiner can assist in the self-optometry properly by entering the responses heard from the examinee on behalf of the examinee.

The self-optometry assistance step may include a continuous resumption step in which the self-optometry that has been temporarily stopped resumes from the next step after the step for which the optometry has already been completed (for example, a completed test). In this case, the self-optometry resumes from the next step after the step for which the optometry has already been completed. Therefore, even after the assistance for the self-optometry has been completed, the self-optometry can properly continue along the progress procedure.

The self-optometry assistance step may include a designated resumption step in which the self-optometry that has been temporarily stopped resumes from a step designated by the examiner (for example, a designated test). In this case, the examiner can resume the self-optometry from the step designated by him/her when a problem that occurred during the self-optometry is resolved, etc. Therefore, burden on the examiner for assisting in the optometry can be prevented from excessively increasing.

The progress procedure for the self-optometry may define multiple tests (examinations) performed on the examinee and an order in which the multiple tests are conducted. At the self-optometry progress step, multiple tests may be performed sequentially in accordance with the progress procedure. In this case, the multiple tests for the examinee can be done automatically and appropriately. Furthermore, the examiner may perform suitable assistance for tests that are determined by the examiner to require for assistance among the multiple tests (for example, a test where a proper correction value cannot be acquired in the self-optometry).

The self-optometry assistance step may include a step for displaying the progress procedure on a display unit. The display unit may be located in a facility where the examiner is waiting, may be located in a different facility than a facility where the self-optometry device is located, or may be located in the same facility where the self-optometry device is located. During the designated resumption step, an instruction for designating a step from which the self-optometry will resume (hereinafter referred to as a "resumption step") for resuming the self-optometry may be accepted through an operation on the progress procedure displayed on the display unit. In this case, the examiner can designate the resumption step to resume the self-optometry while properly recognizing the details and progress status of the progress procedure displayed on the display unit.

Note that a specific methods for accepting the input of the resumption step through an operation on the displayed progress procedure can be appropriately selected. For example, a touch panel may be disposed in a display area of the display unit. In this case, the control unit may treat, as the resumption step designated by the examiner, the step (for example, a specific test) corresponding to the position on the touch panel where the touch panel is operated among the displayed progress procedure. Alternatively, a mouse or the like for moving a pointer within the display area of the display unit may be provided. In this case, the control unit may treat the step corresponding to the position of the pointer on the displayed progress procedure as the resumption step designated by the examiner.

The control unit may display, on the progress procedure, at least one of the step currently being executed or the step during which a problem occurred among the entire progress procedure (e.g., multiple tests included in the progress procedure). In this case, the examiner can properly recognize the progress status of the self-optometry system by the displayed progress procedure.

As described above, resuming the self-optometry that was temporarily stopped leads to obtaining various benefits. For example, in the cross-cylinder test, which is one of the tests performed by the subjective optometry system, two sets of dots are presented to an examinee. However, if the relative position between the examination window of the correction optical system and the subject eye is misaligned, the examinee would be able to recognize only one of the two sets of dots. In this case, the examinee would not be able to conduct the self-optometry. However, according to the present disclosure's subjective optometry system, while the self-optometry is temporarily stopped, the examiner can make an advice to the examinee to adjust the position of the subject eye relative to the examination window, for example, to assist in the progress of the cross-cylinder test. Then, the examinee can resume the self-optometry by himself/herself. Thus, resuming the temporarily stopped self-optometry leads to useful effects for both the examiner and the examinee.

The self-optometry assistance step may be executed based on an instruction inputted to the second information processing device that is connected to the first information processing device via a network. In this case, even if the examiner is located at a remote location away from the examinee, the examiner can properly assist the examinee in the self-optometry from the remote location by inputting instructions to the second information processing device.

If a problem occurs during the progress of the self-optometry (for example, if an instruction for the assistance operation is inputted), the control unit of the first information processing device may output, to the second information processing device, an instruction to execute a call operation to call for the examiner. In this case, even if the examiner is at a remote location away from the examinee, the examiner can easily recognize that a problem occurred during the progress of the self-optometry.

However, the self-optometry assistance step may be executed in response to instructions directly inputted to the first information processing device (for example, instructions inputted to the operation unit of the first information processing device). That is, the examiner located at the location where the subjective optometry device and the first information processing device are installed may input instructions to execute the self-optometry assistance step. In this case, the operation unit (examiner's controller) of the first information processing device used for inputting instructions by the examiner may be a dedicated controller provided in the subjective optometry device, or a general-purpose user interface such as a mouse or a tablet.

Furthermore, when the second information processing device is used, the number of the second information processing devices may be one or more. Similar to the first information processing device, various devices (such as PCs, mobile terminals, or smartphones) can be used as the second information processing device. The second information processing device may be connected, in advance, to the first information processing device when the self-optometry is performed, or may be connected to the first information processing device after a problem occurs during the self-optometry.

When the second information processing device is used, each of the control units of the first and second information processing devices may perform a remote conversation step to assist in conversation between the examiner and the examinee by transmitting and receiving at least audio data (which may include both audio and image data) between the examiner and the examinee. In this case, the examiner located remotely can appropriately assist in the self-optometry by recognizing the examinee's situation through the conversation.

<Setting an Examination Timing for Starting the Assistance Operation>

The self-optometry assistance step may include a receiving step for receiving a calling instruction to execute a call operation for calling for an assistant (for example, an examiner) from an examinee and a calling execution step for executing the call operation based on the calling instruction to execute the call operation received at the receiving step. Furthermore, the self-optometry assistance step may include an examination timing setting step for setting an examination timing for starting the assistance operation so that the assistance operation can start from an examination item for which the self-optometry was performed at the timing the calling instruction to execute the call operation was inputted based on the instruction received at the receiving step. Note that the examination timing for starting the assistance operation is used as the start timing for the assistance operation in the progress procedure (an examination flow) of the optometry. In this case, for example, the examiner can effectively assist the examinee in the self-optometry, allowing the examiner to effectively perform the assistance operation for the examination item for which the examinee had a difficulty in conducting the self-optometry.

One technique for setting the examination timing to the examination item that was performed at the time the calling instruction was inputted is to temporarily stop the progress of the self-optometry when receiving the calling instruction, and then set the examination timing to the examination item that was performed at the time the calling instruction was inputted. It is possible to avoid, for example, a situation where incorrect examination results are obtained because the progress of the self-optometry is temporarily stopped when the calling instruction is inputted. It is also possible to reduce the burden on the examinee.

Furthermore, the technique for setting the examination timing to the examination item that was performed at the timing the calling instruction was inputted is not necessarily limited to the above-described example. For example, the examination item that was performed at the timing the calling instruction was inputted may be stored in a storage device in advance, and the examination timing may be set to the examination item performed at the timing the calling instruction was inputted based on the examination item stored in the storage device. This makes it possible to start the optometry from the examination item performed at the timing the calling instruction was inputted. If the optometry is properly executed, it is possible to proceed with the optometry until assistance by the examiner is performed.

In addition, it is also possible to display an identification display image on a display device to identify the examination item performed at the timing the calling instruction was inputted, so that the examination item performed at the timing the calling instruction was inputted can be selected preferentially. Furthermore, it is also possible to display the examination item stored in the storage device on the display device so that assistance in the optometry can be easily performed.

<Restriction on Response Inputs>

In the response acquisition step, it may restrict inputs of responses that are inputted after the calling instruction was inputted. This can prevent, when the examiner performs assistance, the optometry from proceeding erroneously due to the examinee's mis-operation by restricting the examinee's response inputs, for example. Furthermore, when restarting the self-optometry, the restriction on the response inputs may be removed. This realizes smooth resumption of the self-optometry, for example.

Note that the restriction on response inputs is not necessarily limited to a timing the calling instruction is inputted. In the response acquisition step, it is also possible to restrict response inputs that are inputted after the execution instruction for the assistance operation was inputted. This can prevent the optometry from proceeding erroneously due to the examinee's mis-operation, for example. In other words, as an input of the execution instruction for the assistance operation, it may be a temporal stop instruction for stopping the progress of the self-optometry and executing the assistance operation, in addition to the calling instruction. In this case, the execution instruction for the assistance operation may be inputted by the examinee or the examiner, for example.

<Restriction on Inputs from an Examiner's Controller>

In the self-optometry assistance step, it may be permissible to restrict at least a part of operation inputs from an examiner's controller that is configured for operating the subjective optometry device until the calling instruction is inputted. This can prevent interference with the optometry by the examiner who is not familiar with using the controller and inadvertently touches the controller, for example, by restricting operation inputs from the examiner's controller during the self-optometry.

In this case, when the calling instruction is inputted, the restriction on operation inputs from the examiner controller may be removed. This enables smooth assistance by the examiner when the calling instruction is inputted. Furthermore, when resuming the self-optometry, at least part of operation inputs from the examiner controller may be restricted. Accordingly, an examination after resuming the self-optometry can be performed properly, for example.

Note that the partial restriction on the operation inputs is not necessarily limited to the timing the calling instruction is inputted. For example, during the assistance step, by restricting a part of operation inputs from the examiner controller for controlling the subjective optometry device until the execution instruction for the assistance operation is inputted, an interference with the self-optometry by the examiner who is not familiar with using the controller and inadvertently touches the controller can be prevented. Furthermore, the restriction on the operation inputs may be removed when the execution instruction is inputted. That is, an input of the execution instruction for the assistance operation may include an input of a temporary stop instruction for stopping the progress of the self-optometry and executing the assistance operation, in addition to an input of the calling instruction, for example. In this case, the execution instruction for the assistance operation may be inputted by the examinee or the examiner, for example.

Note that at the self-optometry assistance step, when the execution instruction for the assistance operation is inputted, the restriction on the operation inputs from the examiner controller may be removed but responses from the examinee may be restricted. This enables reliable switching between the self-optometry by the examinee and the assistance operation by the examiner, and prevents each examination from proceeding unexpectedly.

The self-optometry assistance step may include an outputting step for outputting elapsed time from the timing at which the calling instruction was inputted. It is possible to confirm, for example, the elapsed time from the timing at which the calling instruction was inputted.

When the assistance operation is started from the examination item that was performed at the timing the calling instruction was inputted, the self-optometry assistance step may control the subjective device so that the subjective device has the examination state at the timing the calling instruction was inputted. For example, the visual target that was displayed at the timing the calling instruction was inputted may be displayed on a visual target display unit, or the correction value that was set at the timing the calling instruction was inputted may be set in the correction optical system. As a result, for example, since the examination state at the time the call instruction was inputted is maintained, the assistance operation can be smoothly performed from the examination item for which the examinee had a difficulty in proceeding, and thus it is possible to avoid an examination with inappropriate setting.

In this case, for example, the subjective device may be automatically controlled so that the subjective device has the examination state at which the subjective device was at the time the calling instruction was inputted. Alternatively, the examination state at which the device was at the timing the calling instruction was inputted may be displayed on the display device and the examiner may adjust the examination state to the displayed examination state by manual operation of the examiner. Note that by both displaying the visual target and setting the correction value, the examination state at which the device was at the timing the call execution was inputted can be more accurately reproduced. However, either one of displaying the visual target or setting the correction value may be performed.

When performing the assistance operation for an examination item that was performed at the timing the calling instruction was inputted, the self-optometry assistance step may control the subjective device to have an initial state in the examination item. For example, the visual target at the start timing of an examination item that was performed at the timing the calling instruction was inputted may be displayed on the visual target display unit, or the correction value at the start timing in the examination item that was performed at the timing the calling instruction was inputted may be set in the correction optical system. Therefore, for example, it is possible to perform the optometry from the initial state at which the device was at the timing the calling instruction was inputted. If the examination at the timing the calling instruction was inputted was improperly performed, the examination can be reset once, and the optometry can be performed from the beginning, which makes it possible to smoothly perform the optometry. By performing both displaying the visual target and setting the correction value, it is possible to more accurately reproduce the initial state of the examination at the timing the calling instruction was inputted. However, either displaying the visual target or setting the correction value may be performed. In this case, for example, the subjective device may be automatically controlled to have the initial state of the examination item that was performed at the timing the calling instruction was inputted, or the initial state of the examination item that was performed at the timing the calling instruction was inputted may be displayed on the display device and the examiner may adjust it to the displayed initial state of the examination item by manual operation of the examiner.

A correction value (i.e., an initial value) set as an initial state, for example, may be set based on, for example, at least one of data of objectively-measured data, previous eyeglass data, and past subjectively-measured data. For example, a value different from the above-described data may be used as an initial value. In this case, for example, any value (such as a default value, for example, 0) may be set as the initial value.

For example, as the objectively-measured data, data obtained by objectively measuring optical characteristics of an subject eye may be used. In this case, examples of optical characteristics of the subject eye that can be objectively measured may include refractive power (e.g., spherical degree, astigmatic degree, astigmatic axis angle), polarization characteristics, inter-pupillary distance, and the like. Additionally, as an example of the past eyeglass data, data obtained by measuring optical characteristics of eyeglasses worn by an examinee may be used. In this case, examples of optical characteristics of eyeglasses include refractive power (e.g., spherical degree, astigmatic degree, astigmatic axis angle), polarization characteristics, inter-pupillary distance, and the like. Furthermore, as an example of the past subjectively-measured data, subjectively-measured data that are measurement results of the past subjective optometry that was performed by the examinee. In this case, as an example of the subjectively-measured data, data obtained by subjectively measuring optical characteristics of the subject eye may be used. Examples of optical characteristics of the subject eye that can be subjectively measured include refractive power (e.g., spherical degree, astigmatic degree, astigmatic axis angle), polarization characteristics, inter-pupillary distance, and the like.

A first control for controlling the subjective device to have the examination state at which the device was at the timing the calling instruction was inputted, and a second control for controlling the subjective device to have the initial state of the examination item that was performed at the timing the calling instruction was inputted may be selectively executed. In this case, the first control and the second control may be selectable by an examiner through the examiner's controller. This allows the examiner, for example, to perform device setting for performing assistance by the examiner according to the examination state after conducting a hearing on the examination state.

When the examiner selects one of the first control and the second control, the second control may be selected if the optometry was at an initial stage of an examination item when the calling instruction was inputted. On the contrary, the first control may be selected if the optometry was at a final stage of the examination item when the calling instruction was inputted. In this case, if a monocular examination is performed, device setting may be done only for the examined eye. In addition, the examiner may select the desired control as appropriate, and is not necessarily limited to the above-described example.

The self-optometry assistance step may also be performed in response to an instruction inputted to the second information processing device, which is another information processing device connected to the first information processing device via a network. For example, if an examiner is located in a remote location different from the examinee, it may be difficult to understand the progress of the self-optometry and to understand the examination item that was performed at the timing the calling instruction was inputted. Therefore, when starting the assistance operation at the self-optometry assistance step, by setting the examination timing to the examination item that was performed at the timing the calling instruction was inputted, even a remote examiner can smoothly perform the assistance operation for the examinee on the difficult examination item, thereby effectively assisting the examinee in the self-optometry.

Embodiment (System Configuration)

Here, an embodiment of the present disclosure will be described with reference to the drawings. As shown in FIG. 1, a subjective optometry system 100 of the present embodiment includes a subjective optometry device 1 and a first information processing device 2A. The subjective optometry device 1 is used to subjectively measure an optical characteristic of eyes of an examinee. The optical characteristic of the subject eye measured by the subjective optometry device 1 of this embodiment is a refractive power of the eyes. The measured refractive power may be at least one of the spherical power, cylindrical power, and astigmatism axis angle of the subject eye. The first information processing device 2A is connected to the subjective optometry device 1. Hereinafter, the first information processing device 2A may also be referred to as a “connection device”. Furthermore, the first information processing device 2A is connected to a second information processing device 2B, which is another information processing device, via a network 5. That is, the first information processing device 2A of this embodiment may be remotely accessed by the second information processing device 2B. Hereinafter, each device will be described in detail.

Description will be given regarding the subjective optometry device 1. The subjective optometry device 1 includes an eye refractive power measurement unit 10, a visual target presentation unit 15, and a relay unit 19.

The eye refractive power measurement unit 10 includes a correction optical system 11 and a driver 12. The correction optical system 11 changes the optical characteristic of a visual target light flux presented to the subject eye. Specifically, the correction optical system 11 changes at least one of the spherical power, cylindrical power, astigmatic axis angle, polarization characteristic, and aberration amount of the visual target light flux. For example, in this embodiment, the correction optical system 11 switchably selects an optical element to be arranged in an examination window in front of the subject eye among multiple optical elements to change the optical characteristics of the visual target light flux. In this embodiment, a lens disk for the left eye and a lens disk for the right eye, each having multiple optical elements arranged in a common circumferential direction, are used in the correction optical system 11. Each of the lens disks for the left eye and the right eye may be formed of a single lens disk or a plurality of lens disks. Examples of the optical elements include, but are not limited to, spherical lenses, cylindrical lenses, cross-cylinder lenses, rotary prisms, and wavefront modulation elements. The driver 12 drives the correction optical system 11 to change the optical characteristics of the visual target light flux. In this embodiment, the driver 12 drives the correction optical system 11 to switch the optical elements in the examination window by rotating both the lens disks for the left eye and the right eye. A step motor or the like may be used for the driver 12. The driver 12 operates in response to a driving signal.

The visual target presentation unit 15 presents a visual target (for example, a Landolt ring or at least one of characters) to the subject eye and switches visual targets presented to the subject eye. Specifically, the visual target presentation unit 15 includes a visual target presentation portion 16 and a driver 17. The visual target presentation portion 16 presents one of the visual targets to the subject eye. Examples of the visual target presentation portion 16 include a space-saving visual target projecting device that projects a visual target onto the subject eye via a concave mirror, a chart projector that projects the visual target onto a screen, and a display that displays the visual target. The visual target presentation portion 16 is positioned to be away a particular distance (in a meaning of an optical system) from the subject eye and is placed at the same height as the eye refractive power measurement unit 10. The driver 17 drives the visual target presentation portion 16 to switch the visual targets presented to the subject eye. The driver 17 operates in accordance with driving signals.

The relay unit 19 relays driving signals between the first information processing device 2A and the drivers 12, 17. In this embodiment, a system for the driving signals output from the first information processing device 2A and a system for the driving signals for controlling at least one of the drivers 12 and 17 are different. The relay unit 19 in this embodiment converts the driving signals received from the first information processing device 2A into driving signals for controlling the drivers 12 and 17, and transmits them to the drivers 12 and 17. Furthermore, in one example of this embodiment, when the relay unit 19 receives one driving signal from the first information processing device 2A so as to drive both the driver 12 and the driver 17 together, the relay unit 19 converts the received one driving signal into two driving signals to drive both the drivers 12 and 17, and transmits them to the drivers 12 and 17.

The first information processing device 2A and the second information processing device 2B will now be described. The first and second information processing devices 2A and 2B can be any of various information processing devices capable of processing various types of information. For example, personal computers (referred to as “PCs” hereinafter) may be used as the first and second information processing devices 2A and 2B in this embodiment. However, information processing devices that serve as the first and second information processing devices 2A and 2B in this embodiment are not necessarily limited to the PCs. For example, a server, mobile terminal, or smartphone may be used as at least one of the first and second information processing devices 2A and 2B. At least one of the first and second information processing devices 2A and 2B may be formed of multiple devices. For example, the first information processing device 2A may be formed of a personal computer and a dedicated controller having a controller and storage device.

The first information processing device 2A and the second information processing device 2B are communicatably connected to each other via the network (e.g., the Internet) 5. An example shown in FIG. 1 is a case where a plurality of second information processing devices 2B are connected to the single first information processing device 2A. However, one second information processing device 2B may be connected to one first information processing device 2A. Additionally, one second information processing device 2B may be connected to a plurality of first information processing devices 2A.

The first information processing device 2A is installed at a location where a subjective optometry is conducted for an examinee (e.g., an eyeglasses store or hospital). The first information processing device 2A is equipped with a CPU 21A and a storage device 22A. The CPU 21A is a control unit (controller) that controls the first information processing device 2A. The storage device 22A stores programs and various types of data. In this embodiment, the optometry control program is stored in the storage device 22A.

The first information processing device 2A is communicatably connected to the subjective optometry device 1 (more specifically, to the relay unit 19 of the subjective optometry device 1). Various standards, such as LAN, can be used for connection between the first information processing device 2A and the subjective optometry device 1. Additionally, the first information processing device 2A is connected to an objective optometry device 3. The objective optometry device 3 measures optical characteristics of the subject eye (such as spherical power, cylindrical power, and astigmatic axis angle) objectively. Various standards such as LAN can be used for connection between the first information processing device 2A and the objective optometry device 3. Note that the objective optometry device 3 may also be connected to the relay unit 19. The measurement results obtained from the objective optometry device 3 can be stored in a storage device of the relay unit 19.

The first information processing device 2A is connected to a camera 31A, a microphone 32A, a speaker 33A, an operation unit 34A, and a display unit 35A. The camera 31A captures images. Specifically, in this embodiment, the camera 31A is used to capture moving images of the examinee. The microphone 32A converts sound into audio signals and outputs them. The speaker 33A converts audio signals into sound. The operation unit 34A is operated by a user (such as an examinee) to input various instructions. For the operation unit 34A, at least one of a keyboard, a mouse, and a touch panel can be used, or a dedicated operation unit (such as a joystick) suitable for inputting responses for the subjective optometry can be used. The display unit 35A displays various images. Various devices capable of displaying images (such as a monitor, a display, and a projector) can be used as the display unit 35A.

Each of the second information processing devices 2B is located in a facility with an examiner (for example, an eyewear store employee who is knowledgeable in optometry using the subjective optometry device 1, a doctor, or a nurse, etc.) who is capable of performing an optometry using the subjective optometry device 1. Each of the second information processing devices 2B includes a CPU 21B and a storage device 22B. The CPU 21B is a control unit (controller) that controls the second information processing device 2B. The storage device 22B is capable of storing programs and various data, etc.

A camera 31B, a microphone 32B, a speaker 33B, an operation unit 34B, and a display unit 35B are connected to the second information processing device 2B. Various devices can be used as these devices, similar to the devices connected to the first information processing device 2A as described above.

(Program-Optometric Method)

A program installed in the first information processing device 2A of this embodiment will now be described. As described above, the optometry control program for executing an optometry control process (refer to FIG. 2) is stored in the storage device 22A of the first information processing device 2A. The optometry control program includes a drive control program for executing a drive control and a self-optometry program for executing a self-optometry. The drive control program controls operation of the subjective optometry device 1 by transmitting control signals to the subjective optometry device 1. The self-optometry program automatically conducts the optometry by the subjective optometry device 1 based on responses inputted from an examinee. The drive control program and the self-optometry program may be separately formed and prepared, or may be incorporated into a single program.

Herein described is a subjective optometry method that can be performed by the subjective optometry system 100 in the present embodiment. The subjective optometry system 100 of the present embodiment can perform both a self-optometry and a remote-optometry. The self-optometry is an eye examination performed by the self-optometry program. In other words, during the self-optometry, the eye examination proceeds automatically based on responses inputted by an examinee. Furthermore, in the subjective optometry system 100 of the present embodiment, if a problem with the progress of the self-optometry occurs, a self-optometry assistance process is executed to assist the examinee in the progress of the self-optometry. The self-optometry assistance process can also be executed in response to an instruction signal inputted to one of the second information processing devices 2B that is located in a remote location. Therefore, even if a problem with the progress of the self-optometry occurs, the eye examination can smoothly continue. In the following description, the self-optometry will be mainly described.

(Optometry Control Process)

Figure 2:
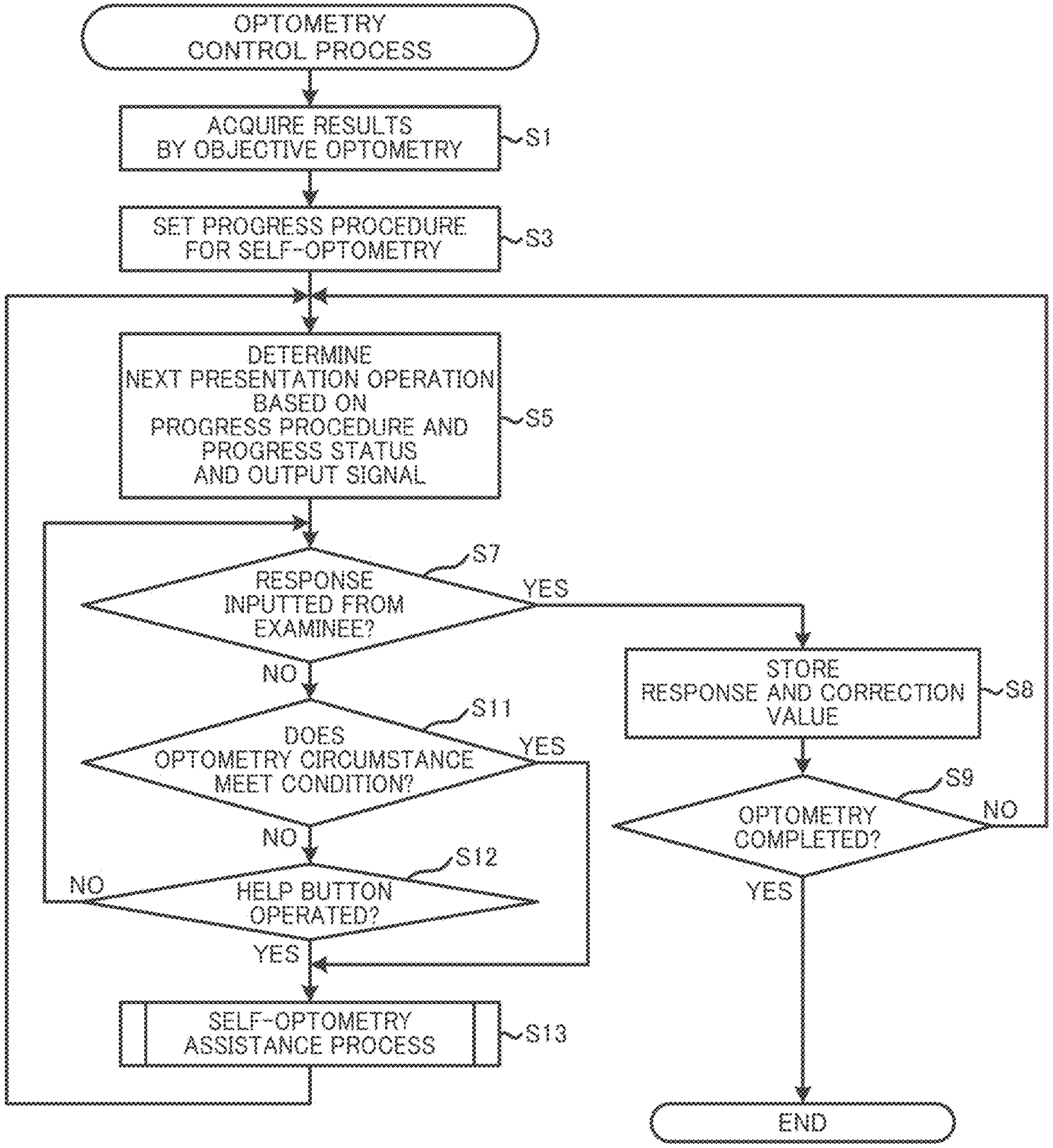
FIG. 2 is a flowchart of an optometry control process executed by a first information processing device 2A.
Figure 3:
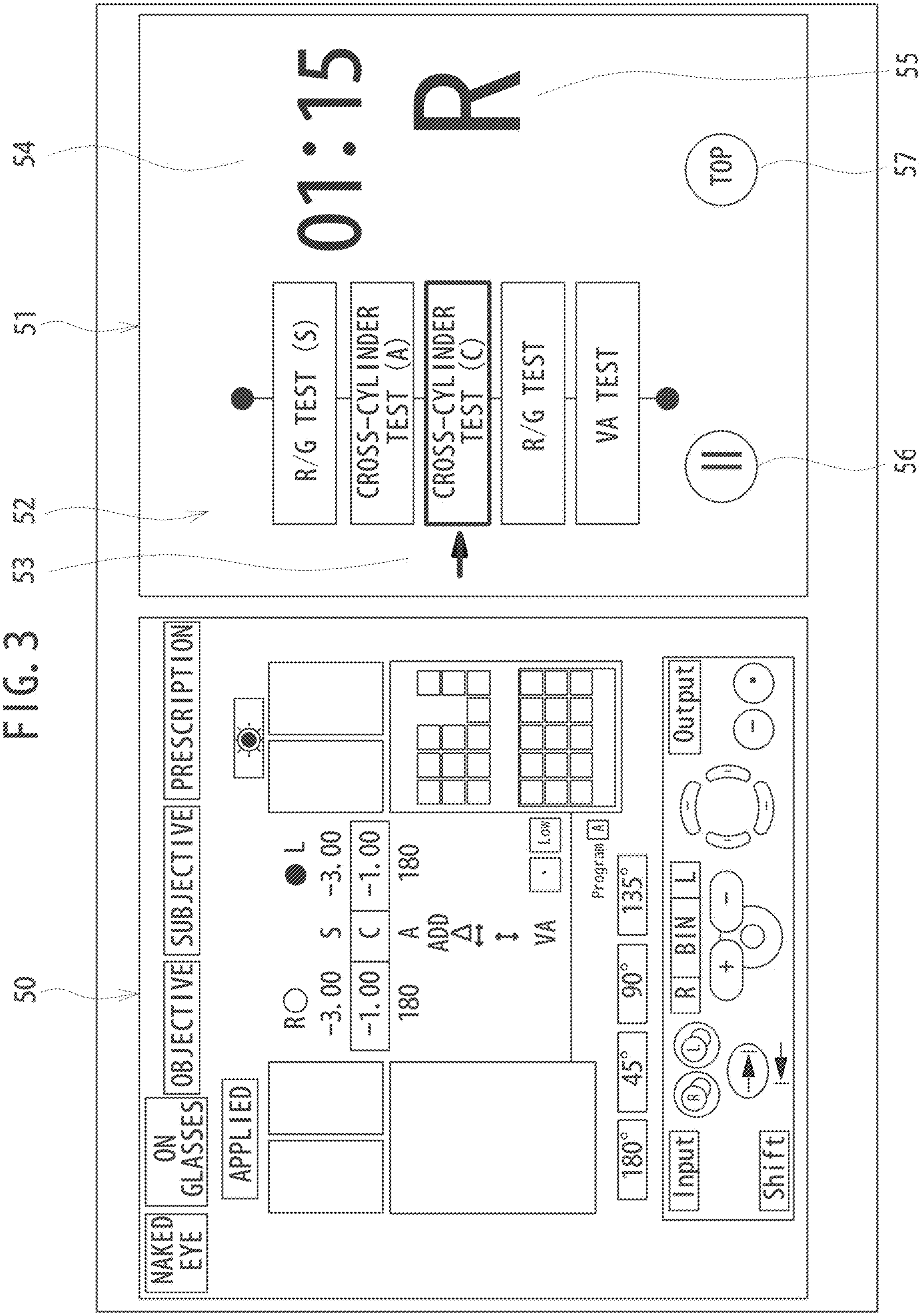
FIG. 3 is a diagram showing an example of a self-optometry assistance screen in the embodiment.
Figure 4:
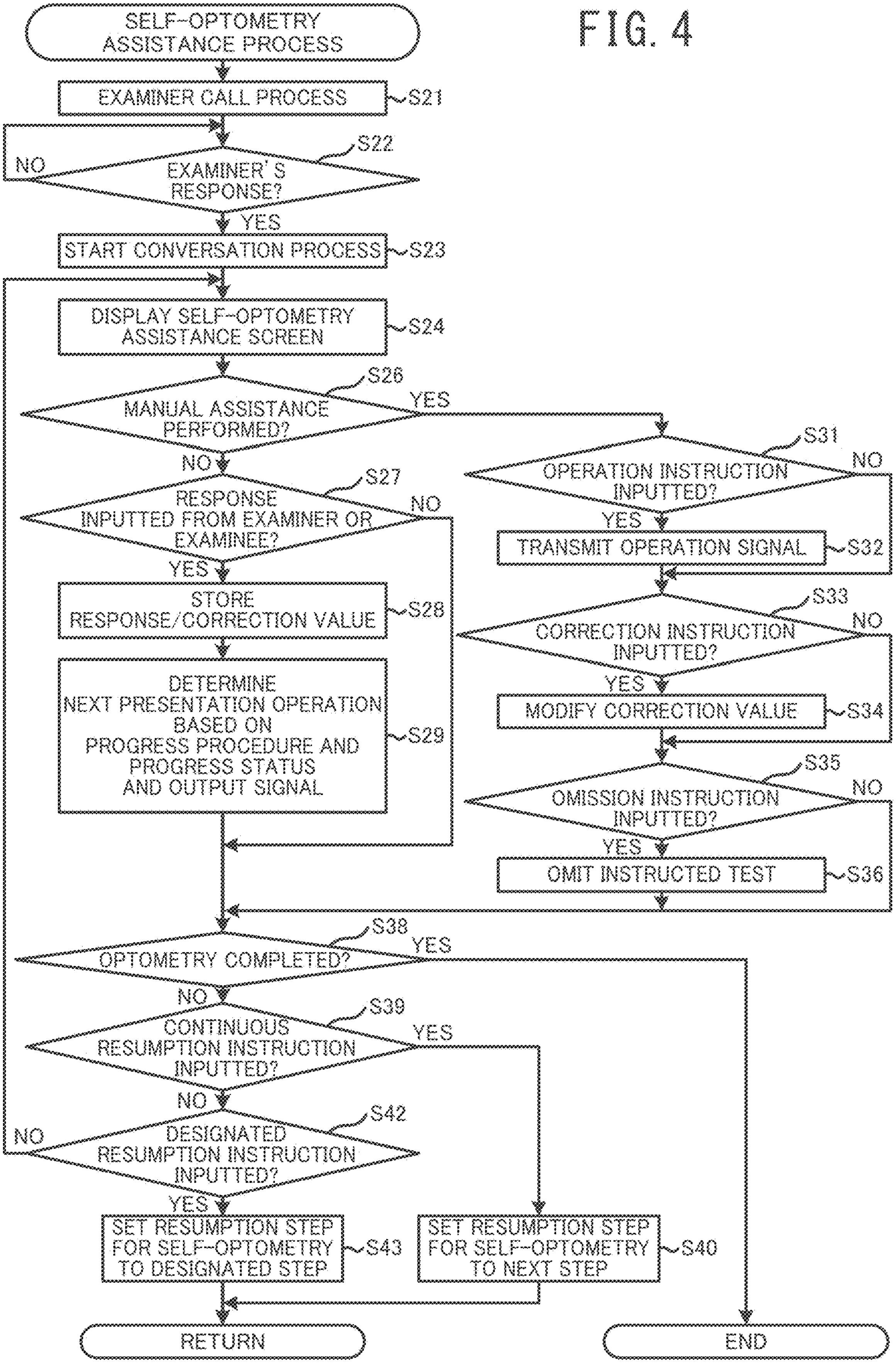
FIG. 4 is a flowchart of a self-optometry assistance process executed during the optometry control process.

Referring to FIGS. 2 to 4, an example of the optometry control process performed by the first information processing device 2A of the subjective optometry system 100 of the present embodiment will be described. The optometry control process includes processing for controlling the self-optometry, processing for assisting in the self-optometry, and the like. When an instruction to start a subjective optometry on an examinee is inputted to the first information processing device 2A, the CPU 21A of the first information processing device 2A executes the optometry control process as illustrated in FIG. 2 according to the optometry control program.

As an example, the optometry control process of the present embodiment is performed when communication (e.g., remote access) between one or more second information processing devices 2B and the first information processing device 2A has been established. However, communication between the first information processing device 2A and one or more of the second information processing devices 2B may also be established during the execution of the optometry control process (e.g., at the timing of starting a self-optometry assistance process illustrated in FIG. 4). The communication method between the first information processing device 2A and the second information processing device 2B may also be appropriately selected. For example, remote access service (RAS) can be used to establish the remote access of the second information processing device 2B to the first information processing device 2A.

First, the CPU 21A acquires results of an externally-conducted objective optometry (S1). For example, in this embodiment, a LAN or the relay unit 19 is used to connect to the external objective optometry device 3 (refer to FIG. 1) to acquire the results of externally-conducted objective optometry for a same examinee. However, the CPU 21A may also acquire results of the externally-conducted objective optometry for the same examinee using, for example, a detachable memory or the network 5. Additionally, results of the externally-conducted objective optometry may also be inputted by the user via the operation unit 34A, etc. If there are no results of the externally-conducted objective optometry for the same examinee, the process at S1 may be skipped.

Next, the CPU 21A sets a progress procedure for the self-optometry (S3). An example of a part of the progress procedure for the self-optometry used in the subjective optometry system 100 of this embodiment is displayed in a progress procedure display field 52 shown in FIG. 3 (the progress procedure for the right eye is only shown in FIG. 3). As shown in FIG. 3, the progress procedure used in this embodiment sets (i) multiple tests (multiple examinations) executed for the examinee and (ii) the order in which these tests are executed. For example, in the progress procedure shown in FIG. 3, after executing R/G test(S), cross-cylinder test (A), cross-cylinder test (C), R/G test, and VA test for the right eye of the examinee, the same tests are executed for the left eye of the examinee in the following order: R/G test(S), cross-cylinder test (A), cross-cylinder test (C), R/G test, and VA test. In the R/G test(S), the spherical power of the subject's eye is measured. In the cross-cylinder test (A), the axis angle of astigmatism of the subject's eye is measured. In the cross-cylinder test (C), the degree of astigmatism of the subject's eye is measured. In the subsequent R/G test, it is confirmed whether an adjustment function of the subject's eye properly worked for the executed tests. In the VA test, the maximum visual acuity of the subject's eye is measured.

At S3, if the results of the objective optometry as to the same examinee were obtained at S1, the progress procedure for the self-optometry is set based on the results of the objective optometry (e.g., the refractive power measured for the subject eye (i.e., spherical power, astigmatic degree, and astigmatic axis angle). For example, in each test included in the procedure, the type and size of the optical element to be first placed in the examination window of the correction optical system 11 and the type of the visual target to be presented on the display unit 16 may be set based on the results of the objective optometry. If the astigmatic degree obtained by the objective optometry falls below a threshold value, a procedure without the test related to astigmatism (e.g., the cross-cylinder test (A) and the cross-cylinder test (C) may be set. At S3, when the results of the objective optometry are not obtained at S1, a default process may be set.

Next, the CPU 21A determines the presentation operation of the visual target to be executed next time by the subjective optometry device 1 based on the progress procedure set at S3 and the progress status of the self-optometry and outputs a presentation instruction signal (i.e., a driving signal) for executing the determined presentation operation to the subjective optometry device 1 (S5). Specifically, at S5 of this embodiment, at least one of the optical elements to be placed in the examination window of the correction optical system 11 and the visual target to be presented on the visual target presentation portion 16 is determined as the next presentation operation. A driving signal for at least one of the drivers 12 and 17 is transmitted to the subjective optometry device 1 to execute the determined operation. Note that when transmitting the driving signal to the subjective optometry device 1, the CPU 21A outputs a guidance voice corresponding to examination contents from the speaker 33A. Therefore, the examinee will see the presented visual target after appropriately understanding the contents of the examination.

In the present embodiment, the driving signal is transmitted from the first information processing device 2A to the drivers 12 and 17 through the relay unit 19 described above (see FIG. 1). Therefore, there is no need for a dedicated controller through which signals transmitted from the first information processing device 2A pass. Thus, signal processing by such a dedicated controller can be omitted, leading to smoother execution of the optometry.

In the self-optometry, the examinee understands the test contents through the guidance audio, visually recognizes the presented visual target displayed on the subjective optometry device 1, and enters its response to the visually recognized visual target into the first information processing device 2A. As an example, in the present embodiment, the dedicatedly-manufactured operation unit (i.e., an examinee controller) 34A suitable for entering responses for the subjective optometry is operated by the examinee to input his/her responses. However, responses may also be input using a general-purpose operation unit 34A, such as a mouse, touch panel, or keyboard. Responses may also be inputted using voice signals converted by the microphone 32A.

The CPU 21A determines whether a response has been inputted from the examinee (S7). When a response has been inputted (S7: YES), the input response and the optical correction value (measurement value) for the specific optical characteristics of the subject eyes are stored in the storage device 22A (S8). The optical correction value for the optical characteristics of the subject eyes is acquired based on the input response at S7, the visual target presented to the examinee when the response was made, and the optical characteristics of the optical element (i.e., the optical characteristics of the visual target light flux) set within the examination window of the correction optical system 11.

If a series of self-optometry processes has not yet been completed (S9: NO), the process returns to S5 and the self-optometry continues in accordance with the progress procedure. For example, in the VA test of this embodiment, if the response from the examinee obtained at S7 is correct, the CPU 21A determines the next visual target presentation operation so that the visual target to be presented next by the visual target presentation portion 16 is an visual target with a visual acuity value one step higher than the previously presented visual target (e.g., a visual target being one step smaller in size). Furthermore, if the response from the examinee obtained at S7 is incorrect, CPU 21A determines the next visual target presentation operation so that the visual target presented by the visual target presentation portion 16 is a visual target with a visual acuity value one step lower than the previously presented visual target (e.g., a visual target being one step larger in size). Also, along with switching of the visual target, the CPU 21A may determine, as the next visual presentation operation, the correction degree of the optical element placed in the examination window of the correction optical system 11.

Note that if the processes at S7 to S9 are repeatedly executed and the entire self-optometry is successfully completed (S9: YES), the optometry control process ends.

If no response is inputted from the examinee (S7: NO), it is determined (S11) whether a predetermined condition that indicates the self-optometry inappropriately proceeds is met. For example, in this embodiment, when a predetermined time has elapsed without a response being inputted from the examinee since the presentation instruction signal was transmitted at S5, the predetermined condition is determined to be met. Furthermore, even if the response inputted by the examinee is inappropriate (e.g., a response other than requested candidate responses is inputted, the same response is inputted continuously more than a predetermined number of times, or more responses than the number requested are inputted), the predetermined condition is determined to be met. If it is determined that the predetermined condition is met (S11: YES), the self-optometry assistance process is executed (S13).

If the response from the examinee is not inputted (S7: NO) and the condition for the self-optometry is not met (S11: NO), the CPU 21A determines whether an instruction for executing an assistance operation for the self-optometry has been inputted by the examinee (S12). For example, in this embodiment, the examinee can input the instruction for executing the assistance operation for the self-optometry by operating a help button 70 provided on the dedicated operation unit (i.e., the examinee controller) 34A or a help button image visually displayed on the display unit 35A. If the instruction is not inputted (S12: NO), the process returns to S7. If the instruction for executing the assistance operation is inputted (S12: YES), the self-optometry assistance process is executed (S13).

Referring to FIG. 4, the details of the self-optometry assistance process will be described. First, the CPU 21A performs an examiner call process (S21). For example, at S21 of this embodiment, the CPU 21A transmits an examiner call instruction via the network 5 to one or more second information processing devices 2B for which remote access to the first information processing device 2A has been established (S4). The examiner call instruction is an instruction for causing the second information processing device 2B to perform a calling action to request an examiner for assistance in the self-optometry. The calling action may be performed by at least one of, for example, outputting sound or displaying an image. By performing the calling action, the user (examiner) of the second information processing device 2B can appropriately understand that assistance in the self-optometry (remote assistance in this embodiment) is requested.

Next, the CPU 21A determines whether there is a response from the examiner, who is a user of the second information processing device 2B (S22). If there is no response from the examiner from any one of the second information processing devices 2B (S22: NO), assistance by the examiner in the self-optometry is not currently available, so the determination process at S22 is repeated and the system waits. If a user of one of the second information processing devices 2B is in a state where he/she can assist in the self-optometry and inputs a response instruction to the one of the second information processing devices 2B (S22: YES), the process proceeds to S23.

Next, the CPU 21A starts communication by transmitting and receiving voice data between the examiner using the second information processing device 2B and the system, thus initiating a conversation process (S23). As a result, the examiner and the examinee can talk, and the assistance process of the self-optometry described below is executed. Specifically, the CPU 21A transmits voice data inputted from the microphone 32A to the second information processing device 2B. In addition, the CPU 21A receives the voice data inputted from the second information processing device 2B through the microphone 32B and outputs it to the speaker 33A. Note that the CPU 21A may also transmit and receive image data to/from the second information processing device 2B along with the voice data. In this case, the CPU 21A may transmit the image data inputted from the camera 31A to the second information processing device 2B. In addition, the CPU 21A may receive the image data inputted from the second information processing device 2B through the camera 32B and display it on the display unit 35A.

Next, the CPU 21A displays a self-optometry assistance screen image (see FIG. 3) on the display unit 35B of the second information processing device 2B used by the examiner who is assisting in the self-optometry (S24). As shown in FIG. 3, the self-optometry assistance screen image in this embodiment includes an operation image area 50 and a progress procedure display area 51.

In the operation image area 50, an operation image including information on the optical characteristics of the visual target light flux presented to the subject eye. In the operation image of this embodiment, values relating to the optical characteristics of the visual target light flux presented to the subject eye are displayed for each type of optical characteristic. The examiner can indicate the value for the desired type of optical characteristic (spherical power, cylindrical power, and astigmatic axis angle, etc.) by operating various buttons and values on the operation image area 50 through an operation device such as a touch panel or a mouse. When the optometry is performed properly, a correction value of the optical characteristic displayed on the operation image area is a measured value of the optical characteristic of the subject eye.

In this embodiment, the progress procedure display area 51 is displayed not only on the display unit 35B connected to the second information processing device 2B but also on the display unit 35A connected to the first information processing device 2A. The progress procedure display area 51 in this embodiment includes the progress procedure display field 52, an elapsed time display field 54, a left/right eye display filed 55, a help button 56, and a top button 57. As mentioned above, the progress procedure set for the ongoing self-optometry is displayed in the progress procedure display field 52. In the example shown in FIG. 3, the test currently being performed among the entire progress procedure (i.e., multiple tests included in the progress procedure) is indicated by an arrow 53 and is emphasized by a bold frame.

The elapsed time display field 54 displays elapsed time since the start of the ongoing self-optometry. The left/right eye display field 55 displays which eye (left or right) of the examinee at the currently performed step among the entire progress procedure is a targeted eye for examination. The help button 56 is operated by the examinee to input an instruction for executing the assistance operation of the self-optometry. The top button 57 is operated to return the screen displayed in the progress procedure display area 51 to the initial page of the self-optometry program.

During the assistance operation of the self-optometry described hereinafter (S24-S43), as mentioned above, the voice signal inputted from the microphone 32A to the first information processing device 2A is converted into sound by the speaker 33B of the second information processing device 2B. Similarly, the voice signal inputted from the microphone 32B to the second information processing device 2B is converted into sound by the speaker 33A of the first information processing device 2A. Therefore, the examiner and the examinee can communicate during the assistance operation of the self-optometry. In addition, during the assistance operation of the self-optometry, the examiner using the second information processing device 2B can input various instructions to assist in operation of the self-optometry using at least one of the operation unit 34B and the microphone 32B.

Next, the CPU 21A determines whether manual assistance by the examiner is being performed (S26). In this embodiment, either indirect assistance or manual assistance is selected as a method for assisting in operation of the self-optometry by the examiner. The indirect assistance is a method in which the examiner indirectly assists in the self-optometry while the self-optometry by the self-optometry program is being performed in accordance with the progress procedure set in S3. The manual assistance is a method for assisting in operation of the self-optometry by directly advancing the examination in response to instructions inputted by the examiner instead of following the self-optometry procedure.

The examiner can control the first information processing device 2A to execute either the indirect assistance or the manual assistance in various ways. For example, in this embodiment, the indirect assistance is set to be executed first when the self-optometry assistance process starts. In addition, the indirect assistance may be switched to the manual assistance by inputting an operation instruction, a correction instruction for modifying the correction value, or an omitting instruction for omitting the procedure into the subjective optometry device 1 through various buttons or the like displayed in the operation image area 50. However, the method for switching from the indirect assistance to the manual assistance can be appropriately selected. For example, a button for switching between the indirect assistance and the manual assistance may be provided on the self-optometry assistance screen.

When the indirect assistance is being performed (S26: NO), the CPU 21A determines whether a response by the examinee who visually recognized the presented visual target has been inputted by the examiner or the examinee (S27). In this embodiment, during the execution of the indirect assistance, the examiner can input the response heard from the examinee into the second information processing device 2B by operating the operation unit 34B connected to the second information processing device 2B. The response inputted to the second information processing device 2B is transmitted to the first information processing device 2A. Therefore, even if the examinee is not familiar with a way of responding for the self-optometry, assisting in the self-optometry can be appropriately performed. In addition, even during the execution of the indirect assistance in this embodiment, as described above, the examinee can also input his/her response by himself/herself (see FIG. 2). Therefore, once the examinee understands the way of responding from an advice by the examiner, it is also possible for the examinee to input the response himself/herself and proceed with the optometry. However, during the execution of the indirect assistance, either the first information processing device 2A or the second information processing device 2B may accept the response.

If the response by the examinee is not inputted into either the first information processing device 2A or the second information processing device 2B (S27: NO), the process proceeds to S38. When the response of the examinee is inputted into the first information processing device 2A or the second information processing device 2B (S27: YES), the inputted response and the optical measurement value of the subject eye are stored in the storage device 22A, similar to S8 (see FIG. 2) (S28). Then, the CPU 21A determines the presentation operation of the visual target to be executed next at the subjective optometry device 1 according to the progress procedure set at S3 (see FIG. 2) and the progress status at that time, and outputs a presentation instruction signal (driving signals) for executing the determined presentation operation to the subjective optometry device 1 (S29). That is, the subjective optometry in accordance with the progress procedure executed by the subjective optometry program continues thereafter. After that, the process proceeds to S38.

Furthermore, if the manual assistance is being executed instead of the indirect assistance (S26: YES), the CPU 21A determines whether an operation instruction for allowing the examiner to manually proceed with at least a part of the progress procedure has been inputted by the examiner (S31). The examiner can determine the operation instruction for the self-optometry device 1, such as an instruction for an arrangement operation of the optical element in the correction optical system 11 and an instruction for a display operation of the visual target in the display unit 16, based on the contents displayed on the self-optometry assistance screen image (see FIG. 3) or the conversation with the examinee. In this case, the examiner inputs the determined operation instruction to the second information processing device 2B via the operation unit 34B or the like. The inputted operation instruction is acquired by the first information processing device 2A via the network 5. When the operation instruction is inputted and acquired (S31: YES), the CPU 21A transmits a display instruction signal (i.e., a driving signal) to the subjective optometry device 1 to execute the instructed operation (S32).

Next, the CPU 21A determines whether an instruction for modifying the correction value stored at S8 (see FIG. 2) or S28 by the self-optometry has been inputted (S33). If the examiner determines that the correction value (i.e., the measured value) displayed on the self-optometry assistance screen image (see FIG. 3) needs to be modified, the examiner inputs a modification instruction for the correction value necessary for modification to the second information processing device 2B via the operation unit 34B or the like. The inputted modification instruction is acquired by the first information processing device 2A via the network 5. When the modification instruction is inputted and acquired (S33: YES), the CPU 21A modifies the correction value according to the instruction (S34).

Then, the CPU 21A determines whether an omission instruction for omitting at least a part of the progress procedure (in this embodiment, at least one of multiple tests) has been inputted (S35). When the omission instruction is inputted via the second information processing device 2B and the network 5 (S35: YES), the CPU 21A omits the instructed test from the progress procedure (S36). Then, the process proceeds to S38.

Next, the CPU 21A determines whether a series of the optometry for the examinee has been completed (S38). For example, the CPU 21A may determine that the series of the optometry has been completed if the self-optometry performed according to the progress procedure has been completed. Alternatively, the CPU 21A may determine that the series of the optometry has been completed when an instruction to end the optometry for the examinee has been inputted. When the series of the optometry has been completed (S38: YES), the process ends.

Next, the CPU 21A determines whether a continuous resumption instruction for the self-optometry has been inputted (S39). The continuous resumption instruction refers to an instruction to resume the self-optometry from the next step after the step for which the optometry has already been completed among the progress procedure set at S3 (see FIG. 2). For example, the CPU 21A may determine that the continuous resumption instruction has been inputted if a continue button (not shown) has been operated by the examinee. When the continuous resumption instruction is inputted via the second information processing device 2B and the network 5 (S39: YES), the CPU 21A sets a resumption step for the self-optometry as a next step subsequent to the step for which the optometry has already been completed among the progress procedure (S40), and the process returns to the optometry control process (see FIG. 2). In the processing of S5 to S9 that follows, the self-optometry is resumed from the resumption step set in S40. When the instruction to continue is not inputted (S39: NO), the process proceeds to S42.

Next, the CPU 21A determines whether a designated resumption instruction for the self-optometry has been inputted (S42). The designated resumption instruction is an instruction to resume the self-optometry from a step designated by the examiner among the progress procedure set at S3 (see FIG. 2). In this embodiment, the examiner can input the designated resumption instruction by designating the resumption step for resuming the self-optometry on the progress procedure displayed in the progress procedure display field 52 in the self-optometry assistance screen image (see FIG. 3). For example, in this embodiment, the examiner can input the designated resumption instruction using a mouse or a touch panel. Note that a designated resumption instruction button (i.e., a reset button) for removing the results of the self-optometry that had been done according to the process procedure and restarting the self-optometry from the first step of the progress procedure may be disposed in the self-optometry assistance display image. When the designated resumption instruction is inputted via the second information processing device 2 and the network 5 (S42: YES), the CPU 21A sets the step designated by the designated resumption instruction among the progress procedure as the resumption point of the self-optometry (S43), and the process returns to the optometry control process (see FIG. 2). In the subsequent processing of S5 to S9, the self-optometry is resumed from the restart step set in S43.

The above-described disclosure in the above embodiment is just one example. Therefore, it is also possible to modify the technology illustrated in the above embodiment. For example, it is possible to execute only a part of the technology illustrated in the above embodiment. The subjective optometry system 100 in the above embodiment executes both the examiner call process (S21) and the self-optometry assistance process by the examiner (S23 to S43) when a problem occurs during the self-optometry (S11: YES or S12: YES). However, the subjective optometry system 100 may execute only one of the examiner call process and the assistance process by the examiner. For example, even if the examiner is called by only executing the examiner calling process, assisting in the self-optometry can be appropriately performed.

In the above embodiment, the self-optometry starts with the second information processing device 2B being connected to the first information processing device 2A. However, after a problem has occurred during the self-optometry (S11: YES or S12: YES), the second information processing device 2B may be connected to the first information processing device 2A.

The self-optometry assistance process of this embodiment (see FIG. 4) is executed in response to the instructions inputted to the second information processing device 2B located remotely. However, the self-optometry assistance process may also be executed in response to an instruction directly inputted to the first information processing device 2A (for example, an instruction inputted to the first information processing device 2A by the operation unit 34A operated by an examiner, etc.). In other words, an examiner at a location where the self-optometry device 1 is installed may input an instruction to assist in the self-optometry. Moreover, both the first information processing device 2A and the second information processing device 2B may accept input of instructions for assisting in the self-optometry. In this case, the examiner can assist in the self-optometry at both the location where the self-optometry device 1 is installed and a remote location. Note that when instructions for assisting in the self-optometry are inputted via the first information processing device 2A, the process of calling for the examiner at S21 (see FIG. 4) may be executed at the first information processing device 2A or may be executed at both the first information processing device 2A and the second information processing device 2B.

Note that at S5 of FIG. 2 and SS29 of FIG. 4, the process of outputting the presentation instruction signal to the self-optometry device 1 based on the progress procedure is an example of the "self-optometry progress step." The process of obtaining a response from the examinee at S7 of FIGS. 2 and S27 of FIG. 4 is an example of a "response acquisition step." The process of storing a correction value in S8 of FIGS. 2 and S28 of FIG. 4 is an example of a "correction value storing step." The self-optometry assistance process shown in FIG. 4 is an example of an "self-optometry assistance step." The process of outputting a presentation instruction signal in response to the operation instruction at S31 and S32 of FIG. 4 is an example of a "manual progress step." The process of modifying the correction value at S33 and S34 of FIG. 4 is an example of a "correction value modification step." The process of omitting progress steps at S35 and S36 of FIG. 4 is an example of a "procedure omission step." The process of obtaining the examinee's response in response to instructions inputted by the examiner at S27 of FIG. 4 is an example of a "proxy response acquisition step". The processing for resuming the self-optometry at S39 and S40 of FIG. 4 is an example of a "continuous resumption step". The processing for resuming the self-optometry according to the step specifically designated by the examiner at S42 and S43 of FIG. 4 is an example of a "designated resumption step". The processing for resuming the self-optometry at S33 and S34 of FIG. 4 is an example of an "self-optometry resumption step". The processing for displaying the progress procedure at S24 of FIG. 4 is an example of a "procedure display step".

<Setting of an Examination Timing Based on a Calling Instruction>

Figure 5:
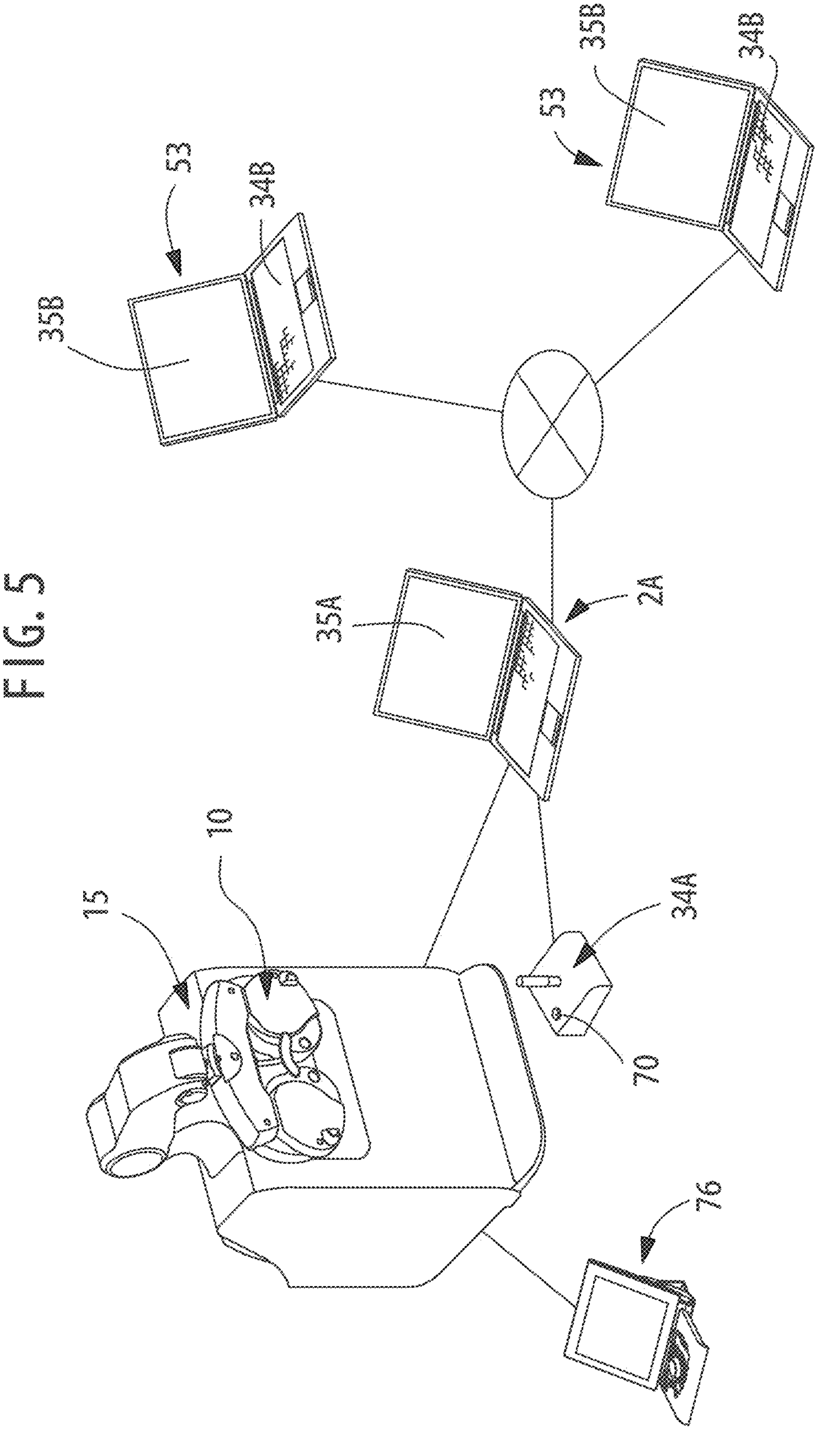
FIG. 5 is a schematic diagram showing one example of the subjective optometry system according to the present embodiment.

The following is an example of execution of the examiner call process. When the help button 70 (for example, refer to FIG. 5) provided on the examinee controller is operated by an examinee, the CPU 21A accepts the input of a calling instruction and performs the examiner call operation.

<Examiner Call>

As the examiner call operation, the CPU 21A may display a calling image for calling for an examiner on a display device (for example, at least one of the display units 35A and 35B). As a manner for displaying the calling image, for example, a message for calling for an examiner (for example, a HELP image 58a in FIG. 6), or a mark for calling for an examiner (for example, a mark 58b in FIG. 6) may be used. Moreover, various types of the calling images such as blinking a display screen image or changing the background of the display screen image may be used, and are not necessarily limited to these examples.

In this case, the display device for displaying the calling image is not necessarily limited to the display units 35A and 35B, but may be a stationary display (i.e., a display device separately disposed from the display unit 35A) installed in a facility with the optometry device, a tablet or smartphone display (i.e., a display separately disposed from the display unit 35A) owned by a staff in the facility, or even another display device that is separately disposed from the display unit 35B that is used remotely. The display device may be a display provided on an examiner controller (for example, the examiner controller 76 or the operation unit 34B shown in FIG. 5), which is operated by the examiner. In other words, the display device is not necessarily a general-purpose display.

In addition, the CPU 21A may generate a calling voice via a voice generating unit as the examiner call operation to call for the examiner, for example. The voice may be, for example, a voice sound calling for a particular examiner by calling his/her name, or a voice sound indicating that the examiner should move to the subjective optometry device. However, the voice is not necessarily limited to these types of voice sounds, and a simple beep sound may be outputted in response to the calling instruction.

Furthermore, the CPU 21A may output the elapsed time from the point when the calling instruction was inputted (see a time image 59 in FIG. 6), for example. For example, the CPU 21A may display the elapsed time together with the calling image for calling for an examiner. In this case, the elapsed time may be outputted by measuring time from the inputted timing of the calling instruction. The manner for displaying the elapsed time is not necessarily limited to the numerical image and the elapsed time may be displayed using various graphics (e.g., indicators) that vary depending on the elapsed time. Also, the outputting method is not necessarily limited to visually displaying the elapsed time. For example, the elapsed time may be outputted as a voice sound.

By outputting the elapsed time as described above, the elapsed time from the inputted timing of the calling instruction can be visualized, which motivates an examiner to perform the optometry assistance as quickly as possible. Also, the assisting examiner can perform appropriate verbal communication according to the elapsed time. For example, if relatively long time has elapsed from the calling instruction, the examiner may choose phrases such as "Sorry for keeping you waiting." Additionally, the examiner can take a measure such as responding preferentially to an examinee who has waited for a longer time than others.

Furthermore, if the CPU 21A detects that the elapsed time exceeds a predetermined time, the CPU 21A may change notification contents based on the detection result. For example, if the elapsed time exceeds the predetermined time, the displaying manner of the calling image may be changed (such as changing color, changing from constant lighting to blinking, etc.). In addition, if the elapsed time exceeds the predetermined time, the louder volume of the calling sound may be outputted.

Furthermore, when outputting the elapsed time from the point the calling instruction was inputted, the CPU 21A may output the elapsed time statistically. For example, the CPU 21A may output the elapsed time for each of plurality of examinees in a tabular form or using graphs. In addition, it may measure the elapsed time for each of plurality of facilities and each of plurality of examiners and output them in a tabular form or using graphs. Accordingly, it is possible to statistically evaluate whether quick responses are made to the calling instructions, and it is possible to promote to make improvements through evaluations for a respective one of the plurality of facilities and/or a respective one of the plurality of examiners.

<Progress Suspension of the Self-Optometry>

When the calling instruction is received, the CPU 21A may temporarily suspend the progress of the self-optometry at the timing the calling instruction is inputted.

In this case, the CPU 21A stops the progress of the optometry with an examination item for which the optometry was performed at the timing the calling instruction was inputted, for example. For instance, the CPU 21A may not accept responses from the examinee after the calling instruction was inputted and may not perform switching to the next correction value and visual target based on the self-optometry program. Thus, the examination state (e.g., the correction value and the visual target) at the time of inputting the calling instruction can be maintained, and the assistance operation by the examiner can be smoothly performed with the maintained examination state. Moreover, by avoiding obtaining an incorrect examination result due to the problem that occurred during the self-optometry by advancing the optometry even after the calling instruction was inputted, the burden on the examinee can be reduced, and the examinee can focus on the optometry under the assistance operation performed by the examiner.

To avoid accepting responses from the examinee, for example, the CPU 21A may restrict inputs of responses of the examinee controller 34A after the calling instruction was inputted. In this case, for example, the CPU 21A may block response signals from the examinee controller 34A, or even though the response signals are accepted, the signals may be ignored without using them for advancing the self-optometry. In this case, it is not necessarily required to restrict all inputs from the examinee controller 34A, and only some inputs of examinee's responses, such as inputting a direction using an input device (e.g., a joystick) or inputting answers whether visual targets are visible, may be restricted.

Furthermore, to avoid switching the correction value and the visual target, inputs of examinee's responses can be restricted as described above. However, the CPU 21A may decide, depending on setting of the self-optometry program, that the visual target is not visible if no response from the examinee is received for certain time period, and then the CPU 21A may switch to the next correction value and visual target. In view of this, by restricting the function of switching the correction value and the visual target after the calling instruction was inputted, it is possible to avoid changing the examination state after the calling instruction was inputted.

The CPU 21A may display an identification display image on the display screen of the display unit that displays the calling instruction so that the examination item for which the optometry was performed at the timing the calling instruction was inputted can be identified. For example, the CPU 21A may emphasize the examination item for which the optometry was performed at the timing the calling instruction was inputted as compared with other examination items (for example, refer to the bold frame display and an arrow 53 in FIG. 6). As another method, for example, the CPU 21A may display the examination item for which the optometry was performed at the timing the calling instruction was inputted in association with displaying the calling instruction. For example, the examination item may be superimposed on the image indicating the calling instruction (for example, the HELP display image 58*a* and the mark 58*b*). Note that the displaying manner for the identification display image can be variously modified and is not necessarily limited to the above examples.

According to the identification display image as described above, the examiner can easily identify the examination item for which the optometry was performed at the timing the calling instruction was input, so that when performing the assistance operation by the examiner, an action in line with the state of the examination item can be performed (for example, the cross-cylinder test as described above).

Furthermore, when the CPU 21A accepts the calling instruction, the CPU 21A may display a display screen corresponding to the examination state at the timing the calling instruction was inputted on the display device (for example, at least one of the display units 35A and 35B and the display of the examiner controller 76) (for example, refer to FIG. 3). Thus, the examiner can confirm not only the examination item preformed at the timing the calling instruction was inputted but also the correction value and the visual target that were set at the timing the calling instruction was inputted, so that an action (for example, selecting the correction value and the visual target) can be taken smoothly when performing the optometry assistance.

When the self-optometry is temporarily suspended, the CPU 21A can immediately stop the progress of the self-optometry upon receiving the calling instruction, thereby immediately avoiding advancing the self-optometry. However, it is not necessarily limited to this way. For example, the CPU 21A may stop the progress of the self-optometry after a predetermined time has elapsed from the timing the calling instruction input was received. In this case, the CPU 21A may stop the progress of the self-optometry when a response is received from the examiner's controller (for example, the examiner's controller 76 shown in FIG. 5, see the operating unit 34B) within a predetermined time after the calling instruction input was received. The above predetermined time may be appropriately set taking into consideration of the program contents of the self-optometry, the examination items, and the like.

In addition, the CPU 21A may be configured to display, on the visual target display unit, an image indicating that the calling instruction is being executed when the calling instruction is inputted. This allows the examinee to easily understand that an examiner is being called.

<Assistance Operation by an Examiner>

When the calling instruction is inputted, the CPU 21A may remove restriction on inputs from the examiner's controller (for example, the examiner's controller 76, the operating unit 34B). In this case, the CPU 21A may restrict at least a part of operation inputs of the examiner's controller until the calling instruction is inputted, and may remove the restriction on the operation inputs of the examiner's controller when the calling instruction is inputted.

When at least a part of the operation inputs is restricted, it is possible to restrict either one of the input from the examiner for operating the correction optical system 11 or the visual target presentation portion 16 or the response input of the examinee by the examiner. When input restriction is made, input signals from the operation unit operated by the examinee can be blocked, or the response itself can be accepted but does not work (ignored) to advance the self-optometry.

During the progress of the self-optometry, the operation inputs of the examiner's controller are restricted until the calling instruction is entered, and therefore, the operation from the examiner's controller is invalidated. This can prevent the response from being inputted or the correction value or visual target from being switched contrary to the procedure of the self-optometry program, even if the examiner inadvertently operates the controller. In this case, it is not necessarily required, even before the calling instruction is inputted, to restrict all operations through the examiner's controller. For example, it is not necessarily required to restrict the function of the inputting device that receives inputs to forcibly perform assistance by an examiner or the function of the inputting device through which an examiner provides an advice to the examinee by voice guidance or guidance messages.

When the calling instruction is entered, the restriction on the operation inputs through the examiner's controller is removed and operations through the examiner's controller become effective. Therefore, the examiner can assist the examinee in the optometry by operating the examiner's controller. For example, the examiner can input responses of the examinee's verbal answer to the examiner's controller, switch the visual target or correction value, and perform other operations on behalf of the examinee.

When the CPU 21A receives the calling instruction, it can quickly assist in the optometry by immediately removing the restriction on the operation inputs through the examiner controller. However, it is not necessarily limited to only this example. For example, the CPU 21A may remove the restriction on the operation inputs through the examiner controller after a predetermined time has elapsed since the calling instruction was inputted. Additionally, if a response is received from the examiner controller indicating that the examiner will perform the assistance, the CPU 21A may also remove the restriction on the operation inputs through the examiner controller.

Figure 6:
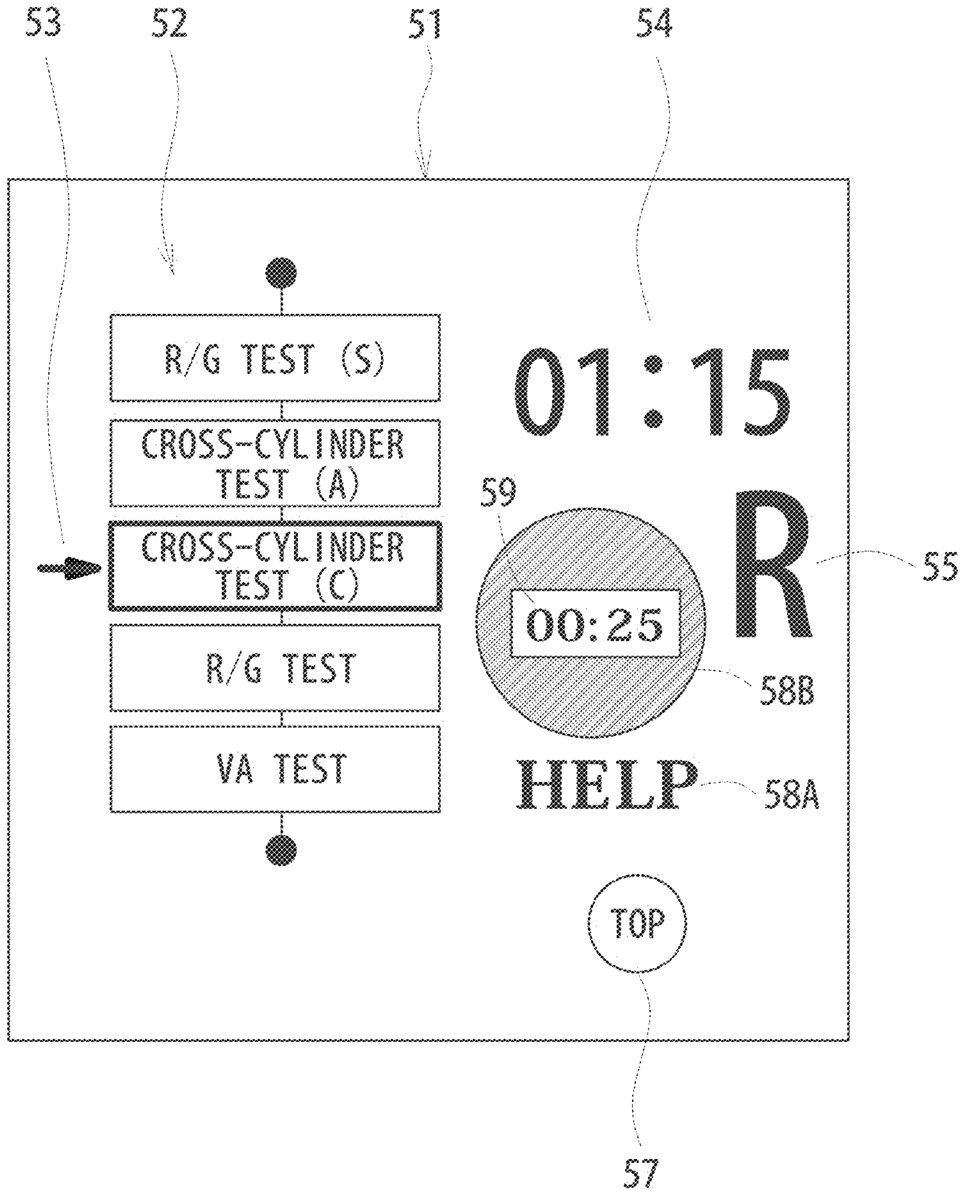
FIG. 6 is a diagram showing one example of a display screen during the self-optometry assistance process.

As a procedure for the assistance operation performed by the examiner, for example, a notification operation for calling for the examiner is performed, and when the examiner is ready to perform the optometry assistance for the examinee, the examiner operates a response switch to indicate the examiner will perform the assistance. When the response switch is pressed, the CPU 21A terminates the examiner call operation. The mark 58*b* may also be used as the response switch as shown in FIG. 6, and when the mark 58*b* is touched, a response signal of the examiner may be inputted. The configuration of the response switch is not necessarily limited to this example, and a physical switch may also be used.

The examiner may operate the examiner controller while viewing the display screen of the display device (for example, at least one of the display unit 35A, the display unit 35B, or the display of the examiner controller 76) that is used for assistance for the examinee. For example, the CPU 21A may display a flow in which multiple examination items based on the self-optometry program are arranged on the display device (see FIG. 6, for example). For example, the examiner can easily select an examination item for which the optometry assistance is to be performed using the examiner controller by select the desired examination item on the display screen. As a result, the examiner can perform the selected examination item of the optometry.

In the self-optometry assistance step described above, the CPU 21A stops the progress of the self-optometry when the calling instruction is inputted, thereby maintaining the examination item performed at the timing the calling instruction is inputted. As a result, the CPU 21A can set an examination timing to the examination item that was performed at the timing the calling instruction was inputted. The examiner can easily select the examination item, which was performed at the timing of inputting the calling instruction, as an examination item for performing the optometry assistance by utilizing the identification display image indicating the examination item that was performed when the calling instruction was inputted. Therefore, the examination timing is set to the examination item that was performed when the calling instruction was inputted.

In this case, by performing the optometry assistance from the examination item for which the optometry was suspended at the timing the calling instruction was inputted, it is possible to perform the optometry assistance from the examination item during which a problem is likely to have occurred during the self-optometry. Therefore, for example, the examiner can easily trace the examinee's memory regarding the examination item performed at the timing of receiving the calling instruction. That is, if the examinee is not familiar with the way of answering to the examination item, the examiner can provide an advisory explanation on how to answer to the examination item. Further, if the examinee is completely invisible to the visual target, the examiner can make an advice on how to view the target through the examination window. Also, it is possible for the examiner to adjust the correction value if the correction value deviates significantly from the examinee's subjective value.

If the self-optometry continues to proceed even after the calling instruction was inputted, the self-optometry would proceed to another examination item different from the item during which some problem is likely to have occurred. In such case, necessary treatment would not be done for the examination item during which the problem has occurred. Furthermore, it may be assumed where the self-optometry proceeds at an examination item at which some problem is likely to have occurred, and as a result, the correction value would significantly deviate from an appropriate subjective value of the examinee. As a consequence, it would take unnecessary longer time to complete the optometry. In view of the above, by setting the examination timing to the temporarily suspended item, the above-described problems can be prevented from occurring.

Even if the selection of the examination item is not performed in the above-described embodiment, the optometry by the examiner may be restarted. For example, the CPU 21A may displays, on a display device (for example, at least one of the display units 35A, 35B, and the display of the examiner controller 76), a display screen indicating the examination state at which the optometry was performed when the calling instruction was inputted. Then, the CPU 21A may accept inputs of responses based on operation signals inputted from the examiner controller or may switch the visual target and the correction value.

Modification Examples

In the above embodiment, the progress of the self-optometry was temporarily stopped when the calling instruction was inputted and the examination timing was set to the examination item that was performed when the calling instruction was inputted. However, it is not necessarily limited to this example. For example, at the self-optometry assistance step, the examination item that was performed when the calling instruction was inputted may be stored in the storage device 22A, and the examination timing may be set to the examination item stored in the storage device 22A that was performed at the time the calling instruction was inputted.

For example, the CPU 21A may, in the storage device 22A, store the examination item that was performed at the timing the calling instruction was inputted and control the display device (for example, at least one of the display units 35A, 35B and the display of the examiner controller 76) to display the identification display image that identifies the examination item that was performed at the timing the calling instruction was inputted based on the examination item stored in the storage device 22A. Accordingly, the examiner can set an examination timing to the examination item that was performed at the timing the calling instruction was inputted based on the identification display image. In addition, when a predetermined operation input is received from the examiner, the CPU 21A may display the examination item on the display device (for example, at least one of the display units 35A, 35B and the display of the examiner controller 76) based on the examination item stored in the storage device 22A.

Even if the examination timing is not set based on the above screen display, the CPU 21A may automatically set the examination timing to the examination item stored in the storage device 22A based on an operation signal from the examiner's controller, when assistance is provided to the examinee.

In the above modification example, the self-optometry may purposely continue without temporarily stopping the progress of the self-optometry even when the calling instruction is inputted. In this case, if the optometry is performed appropriately, more examination results can be obtained until the examiner's assistance begins. Thus, the entire examination time may be shortened. However, it is necessary to consider a possibility of obtaining incorrect examination results. Thus, it should be better to consider the difficulty of the optometry and other factors before deciding whether to implement this approach.

Note that in the above embodiment, the visual target and the correction value that were set at the timing the calling instruction was inputted are set. However, it is not necessarily limited to this example, and smooth assistance for the optometry can be realized by setting the visual target and the correction value corresponding to the examination item that was performed at the timing the calling instruction was inputted.

For example, the CPU 21A may be configured to set the visual target and the correction value that were set at the start timing of the examination item that was performed when the calling instruction was inputted. In this case, the CPU 21A may store the visual target and the correction value that were set at the start timing of the examination item in the storage device 22A in advance. Then, the CPU 21A may set the visual target and the correction value based on those stored in the storage device 22A. By doing so, if the optometry at the timing the calling instruction is inputted is improperly performed, the optometry can be reset and performed from the beginning of the optometry. As a result, the optometry can be performed smoothly. Such control is more advantageous, for example, if the correction value significantly deviates from the subjective value during the self-optometry by the examinee.

Note that the visual target and the correction value at the start timing of the optometry are not necessarily completely identical. For example, a different visual target with the same visual acuity value as the start timing of the optometry may be used. Regarding the correction value, the spherical degree may be the same as one used at the start timing of the optometry, but the astigmatic axis and astigmatic axis angle may be different from those used at the start timing of the optometry. It should be noted that, when setting the visual target and the correction value at the timing the calling instruction was inputted is made, the visual target and the correction value are not necessarily completely identical with those at the timing of inputting the calling instruction.

Also, before the calling instruction is inputted, a monitoring screen for the examiner to monitor the progress of the self-optometry (for example, the presented visual target, the correction value, the response contents, etc.) may be displayed on the display device (for example, at least one of the display units 35A, 35B and the display of the examiner's controller 76). For example, the examiner can easily grasp the progress of the self-optometry in real-time by monitoring the presented visual target and the correction value. Additionally, by displaying the response contents from the examinee, the examiner can easily determine whether the examinee's response is appropriate or not. Furthermore, when the calling instruction is inputted, a calling image for calling for an examiner may be displayed on the monitoring screen. By doing so, when the examination timing is set to the examination item that was performed at the timing the calling instruction was inputted, the examiner can start providing optometry assistance for the examinee while grasping the progress of the self-optometry in advance. As a result, more appropriate assistance can be provided.

In the above embodiment, the examination timing for the assistance operation was set to the examination item that was performed at the timing the calling instruction was inputted. However, the examination timing for starting the assistance operation may be set to an examination item different from the examination item that was performed at the timing the calling instruction was inputted. For example, in the self-optometry of visual acuity, if the calling instruction is inputted while performing the astigmatic axis examination in a cross-cylinder test, it may be better for the examiner to start the optometry from examining the degree of astigmatism in the cross-cylinder test as the assistance operation. In this case, multiple examination items arranged based on the self-optometry program are displayed as a flow on the display screen, and a desired examination item (for example, the astigmatism examination in the cross-cylinder test) is selected by the examiner using the examiner's controller on the display screen, thereby smoothly performing the assistance operation.

In the above description, the calling instruction was defined as an instruction to call for an examiner, but it may be an instruction to call for an assistant. The assistant may include, for example, another examiner who performs a subjective optometry, a staff who does not perform the optometry, and an accompanying person of the examinee. Even when a call is made to a staff or an accompanying person, they are notified of necessity of assistance in the optometry, and therefore an examiner who can perform a subjective optometry can be called through the staff, etc. Furthermore, even a staff can make certain advice, such as adjusting the positional relationship between the optometry device and the examinee.

In the above description, the examination timing was set to the examination item that was performed at the timing the calling instruction was inputted, but it is not necessarily limited to this example. For example, the CPU 21A may be configured to set the examination timing to an examination item that was performed at the timing a situation of the self-optometry satisfied a predetermined condition. With this configuration, assistance of the optometry for the examinee can be smoothly performed from the examination item that was performed at the timing the situation of the self-optometry satisfied the predetermined condition, for example, when a problem is determined to have occurred with the examinee.

In the above description, it is not necessarily limited to removing restriction on inputs of responses from the examinee via the examinee controller after the calling instruction was inputted, but when the examiner performs an optometry assistance, operation to remove the restriction via the examiner controller may be accepted. Accordingly, restriction on inputs of the examinee's response via the examinee controller can be removed. In this case, the examiner can train the examinee on how to input responses or confirm the appropriateness of the responses from the examinee, and thereafter resume the suspended self-optometry.

The above-described embodiments may include the following technical aspects.

One aspect of the present disclosure is a method for a subjective optometry system including a subjective optometry device and a first information processing device connected to the subjective optometry device. The subjective optometry device includes a correction optical system that is configured to change an optical characteristic of a visual target light flux presented to a subject eye and a visual target presentation unit that is configured to present a visual target to the subject eye. The subjective optometry device subjectively measuring an optical characteristic of the subject eye. The method, implemented by the first information processing device, comprises:

controlling the correction optical system and the visual target presentation unit to perform a plurality of examination items in accordance with a progress procedure for the self-optometry that automatically proceeds;

acquiring a response inputted by the examinee who visually recognized the presented visual target; and executing an assistance operation to assist in a progress of the self-optometry when a problem occurs during the progress of the self-optometry.

The method further includes:

receiving, from the examinee, an input of a calling instruction for executing a calling operation to call for an assistant;

executing the calling operation based on the received calling instruction received; and setting, based on the received calling instruction, an examination timing for the assistance operation such that the assistance operation starts from an examination item among the plurality of examination items that was performed at a timing the calling instruction was inputted.

A second aspect of the present disclosure is a method for a subjective optometry system including a subjective optometry device and a first information processing device connected to the subjective optometry device. The subjective optometry device includes a correction optical system that is configured to change an optical characteristic of a visual target light flux presented to a subject eye and a visual target presentation unit that is configured to present a visual target to the subject eye. The subjective optometry device subjectively measures an optical characteristic of the subject eye. The method, implemented by the first information processing device, comprises:

controlling the correction optical system and the visual target presentation unit to perform a plurality of examination items in accordance with a progress procedure for the self-optometry that automatically proceeds;

acquiring a response inputted by the examinee who visually recognized the presented visual target; and executing an assistance operation to assist in a progress of the self-optometry when a problem occurs during the progress of the self-optometry.

The method further comprises:

receiving an input of an execution instruction for executing the assistance operation; and restricting an input of the response that is inputted after receiving the execution instruction.

A third aspect of the present disclosure is a method for a subjective optometry system including a subjective optometry device and a first information processing device connected to the subjective optometry device. The subjective optometry device includes a correction optical system that is configured to change an optical characteristic of a visual target light flux presented to a subject eye and a visual target presentation unit that is configured to present a visual target to the subject eye. The subjective optometry device subjectively measures an optical characteristic of the subject eye. The method, implemented by the first information processing device, comprises:

controlling the correction optical system and the visual target presentation unit to perform a plurality of examination items in accordance with a progress procedure for the self-optometry that automatically proceeds;

acquiring a response inputted by the examinee who visually recognized the presented visual target; and executing an assistance operation to assist in a progress of the self-optometry when a problem occurs during the progress of the self-optometry.

The method further comprises:

receiving an input of an execution instruction for executing the assistance operation;

restricting, until the execution instruction is inputted, at least a part of an operation input from an examiner controller that is configured to control the subjective optometry device by an examiner as the assistant; and removing the restriction on the operation input from the examiner controller when receiving the execution instruction.

The invention claimed is:

1. A non-transitory, computer readable, tangible storage medium storing an optometry control program for a subjective optometry system including a subjective optometry device and a first information processing device connected to the subjective optometry device, the subjective optometry device including a correction optical system that is configured to change an optical characteristic of a visual target light flux presented to a subject eye and a visual target presentation unit that is configured to present a visual target to the subject eye, the subjective optometry device subjectively measuring an optical characteristic of the subject eye, the program being executed by the first information processing device and comprising:

a self-optometry program that causes a self-optometry to proceed automatically based on a response from an examinee, wherein the self-optometry program, when executed by the first information processing device, causes the first information processing device to perform:

controlling the correction optical system and the visual target presentation unit to perform a plurality of examination items in accordance with a progress procedure for the self-optometry that automatically proceeds;

acquiring a response inputted by the examinee who visually recognized the presented visual target; and executing an assistance operation to assist in a progress of the self-optometry when a problem occurs during the progress of the self-optometry, wherein the self-optometry program further causes the first information processing device to perform:

receiving, from the examinee, an input of a calling instruction for executing a calling operation to call for an assistant;

executing the calling operation based on the received calling instruction received; and setting, based on the received calling instruction, an examination timing for the assistance operation such that the assistance operation starts from an examination item among the plurality of examination items that was performed at a timing the calling instruction was inputted, wherein the self-optometry program further causes the first information processing device to perform restricting, after the calling instruction was inputted, an input of the response from the examinee that is a response to the visual target presented to the examinee who visually recognized the visual target and is inputted after the calling instruction was inputted to prevent the self-optometry from automatically proceeding by restricting the input of the response.

2. The medium according to claim 1, wherein the self-optometry program further causes the first information processing device to perform setting the examination timing to the examination item that was performed at the timing the calling instruction was inputted by temporarily stopping the self-optometry at the timing the calling instruction was inputted.

3. The medium according to claim 1, wherein the self-optometry program further causes the first information processing device to perform:

storing, in a storage device, the examination item that was performed at the timing the calling instruction was inputted; and setting, based on the examination item stored in the storage device, the examination timing to the examination item that was performed at the timing the calling instruction was inputted.

4. The medium according to claim 1, wherein the self-optometry program further causes the first information processing device to perform:

restricting, until the calling instruction is inputted, at least a part of an operation input from an examiner controller that is configured to operate the subjective optometry device by an examiner as the assistant; and removing the restriction on the operation input from the examiner controller when the calling instruction is inputted.

5. The medium according to claim 1, wherein the self-optometry program further causes the first information processing device to perform outputting an elapsed time since the calling instruction was inputted.

6. The medium according to claim 1, wherein the self-optometry program further causes the first information processing device to perform the assistance operation in response to an instruction inputted into a second information processing device that is another information processing device connected to the first information processing device via a network.

7. The medium according to claim 1, wherein when starting the assistance operation from the examination item that was performed at the timing the calling instruction was inputted, the self-optometry program further causes the first information processing device to perform at least one of:

presenting, with the visual target presentation unit, the visual target that was presented at the timing the calling instruction was inputted; or setting, with the correction optical system, a correction value that was set at the timing the calling instruction was inputted.

8. The medium according to claim 1, wherein when starting the assistance operation from the examination item that was performed at the timing the calling instruction was inputted, the self-optometry program further causes the first information processing device to perform at least one of:

presenting, with the visual target presentation unit, the visual target that was presented at a start timing of the examination item that was performed at the timing the calling instruction was inputted; or setting, with the correction optical system, a correction value that was set at the start timing of the examination item that was performed at the timing the calling instruction was inputted.

9. A non-transitory, computer readable, tangible storage medium storing an optometry control program for a subjective optometry system including a subjective optometry device and a first information processing device connected to the subjective optometry device, the subjective optometry device including a correction optical system that is configured to change an optical characteristic of a visual target light flux presented to a subject eye and a visual target presentation unit that is configured to present a visual target to the subject eye, the subjective optometry device subjectively measuring an optical characteristic of the subject eye, the program being executed by the first information processing device and comprising:

a self-optometry program that causes a self-optometry to proceed automatically based on a response from an examinee, wherein the self-optometry program, when executed by the first information processing device, causes the first information processing device to perform:

controlling the correction optical system and the visual target presentation unit to perform a plurality of examination items in accordance with a progress procedure for the self-optometry that automatically proceeds;

acquiring a response inputted by the examinee who visually recognized the presented visual target; and executing an assistance operation to assist in a progress of the self-optometry when a problem occurs during the progress of the self-optometry, wherein the self-optometry program further causes the first information processing device to perform:

receiving an input of an execution instruction for executing the assistance operation; and restricting an input of the response that is a response to the visual target presented to the examinee who visually recognized the visual target and is inputted after receiving the execution instruction to prevent the self-optometry from automatically proceeding by restricting the input of the response.

10. A non-transitory, computer readable, tangible storage medium storing an optometry control program for a subjective optometry system including a subjective optometry device and a first information processing device connected to the subjective optometry device, the subjective optometry device including a correction optical system that is configured to change an optical characteristic of a visual target light flux presented to a subject eye and a visual target presentation unit that is configured to present a visual target to the subject eye, the subjective optometry device subjectively measuring an optical characteristic of the subject eye, the program being executed by the first information processing device and comprising:

a self-optometry program that causes a self-optometry to proceed automatically based on a response from an examinee, wherein the self-optometry program, when executed by a controller of the first information processing device, causes the first information processing device to perform:

controlling the correction optical system and the visual target presentation unit to perform a plurality of examination items in accordance with a progress procedure for the self-optometry that automatically proceeds;

acquiring a response inputted by the examinee who visually recognized the presented visual target; and executing an assistance operation to assist in a progress of the self-optometry when a problem occurs during the progress of the self-optometry, wherein the self-optometry program further causes the first information processing device to perform:

receiving an input of an execution instruction for executing the assistance operation;

restricting, until the execution instruction is inputted, at least a part of an operation input from an examiner controller that is configured to control the subjective optometry device by an examiner as the assistant;

removing the restriction on the operation input from the examiner controller when receiving the execution instruction; and restricting, after the execution instruction was inputted, an input of the response from the examinee that is a response to the visual target presented to the examinee who visually recognized the visual target and is inputted after the execution instruction was inputted to prevent the self-optometry from automatically proceeding by restricting the input of the response.

11. A subjective optometry system, comprising:

a subjective optometry device; and a first information processing device connected to the subjective optometry device, wherein the subjective optometry device includes a correction optical system that is configured to change an optical characteristic of a visual target light flux presented to a subject eye and a visual target presentation unit that is configured to present a visual target to the subject eye, the subjective optometry device is configured to subjectively measure an optical characteristic of the subject eye, the first information processing device is configured to execute a self-optometry program that causes a self-optometry to proceed automatically based on a response from an examinee, wherein the first information processing device is, by executing the self-optometry program, configured to:

control the correction optical system and the visual target presentation unit to perform a plurality of examination items in accordance with a progress procedure for the self-optometry that automatically proceeds;

acquire a response inputted by the examinee who visually recognized the presented visual target; and execute an assistance operation to assist in a progress of the self-optometry when a problem occurs during the progress of the self-optometry, wherein the first information processing device is, by executing the self-optometry program, further configured to:

receive, from the examinee, an input of a calling instruction for executing a calling operation to call for an assistant;

execute the calling operation based on the received calling instruction;

set, based on the received calling instruction, an examination timing for the assistance operation such that the assistance operation starts from an examination item among the plurality of examination items that was performed at a timing the calling instruction was inputted; and restrict, after the calling instruction was inputted, an input of the response from the examinee that is a response to the visual target presented to the examinee who visually recognized the visual target and is inputted after the calling instruction was inputted to prevent the self-optometry from automatically proceeding by restricting the input of the response.

12. The subjective optometry system according to claim 11, further comprising a second information processing device that is another information processing device connected to the first information processing device via a network, wherein the first information processing device is further configured to perform the assistance operation in response to an instruction inputted into the second information processing device.

* * * * *